United States Patent
Morris et al.

(10) Patent No.: US 6,458,530 B1
(45) Date of Patent: Oct. 1, 2002

(54) SELECTING TAG NUCLEIC ACIDS

(75) Inventors: Macdonald S. Morris, Felton, CA (US); Daniel D. Shoemaker, Stanford, CA (US); Ronald W. Davis, Palo Alto, CA (US); Michael P. Mittmann, Palo Alto, CA (US)

(73) Assignee: Affymetrix Inc., Santa Clara, CA (US)

( * ) Notice: Subject to any disclaimer, the term of this patent is extended or adjusted under 35 U.S.C. 154(b) by 0 days.

(21) Appl. No.: 08/626,285

(22) Filed: Apr. 4, 1996

(51) Int. Cl.[7] .................... C12Q 1/68; C07H 21/00
(52) U.S. Cl. .................... 435/6; 436/501; 536/23.1; 536/24.2; 536/24.3; 536/24.31; 536/24.32; 536/25.3
(58) Field of Search .................... 435/6, 810; 436/501; 536/23.1, 24.1, 24.2, 24.3–24.33, 25.3; 935/77, 78

(56) References Cited

U.S. PATENT DOCUMENTS

| | | | |
|---|---|---|---|
| 4,683,202 A | * 7/1987 | Mullis | 435/91 |
| 4,719,179 A | 1/1988 | Barany | 435/172.1 |
| 5,002,867 A | 3/1991 | Macevicz | 435/6 |
| 5,143,854 A | 9/1992 | Pirrung et al. | 436/518 |
| 5,149,625 A | 9/1992 | Church et al. | 435/6 |
| 5,200,051 A | 4/1993 | Cozzette et al. | 204/403 |
| 5,210,203 A | 5/1993 | Musso et al. | 548/130 |
| 5,340,728 A | * 8/1994 | Grosz et al. | 435/91.2 |
| 5,384,261 A | 1/1995 | Winkler et al. | 436/518 |
| 5,391,480 A | 2/1995 | Davis et al. | 435/6 |
| 5,412,087 A | 5/1995 | McGall et al. | 536/24.3 |
| 5,429,807 A | 7/1995 | Matson et al. | 422/131 |
| 5,445,934 A | 8/1995 | Fodor et al. | 435/6 |
| 5,451,505 A | * 9/1995 | Dollinger | 435/6 |
| 5,494,810 A | 2/1996 | Barany et al. | 435/91.52 |
| 5,604,097 A | * 2/1997 | Brenner | 435/6 |
| 5,635,400 A | 6/1997 | Brenner | 435/320.1 |
| 5,643,728 A | 7/1997 | Slater et al. | 435/6 |
| 5,654,413 A | 8/1997 | Brenner | 536/22.1 |
| 5,700,637 A | 12/1997 | Southern | 435/6 |
| 5,776,737 A | 7/1998 | Dunn | 435/91.1 |
| 5,800,992 A | 9/1998 | Fodor et al. | 435/6 |
| 5,846,719 A | 12/1998 | Brenner et al. | 435/6 |
| 5,856,092 A | 1/1999 | Dale et al. | 435/6 |
| 5,888,737 A | 3/1999 | DuBridge et al. | 435/6 |
| 5,981,176 A | 11/1999 | Wallace | 435/6 |
| 6,013,445 A | 1/2000 | Albrecht et al. | 435/6 |
| 6,054,270 A | 4/2000 | Southern | 435/6 |
| 6,172,214 B1 | 1/2001 | Brenner | 536/24.3 |
| 6,172,218 B1 | 1/2001 | Brenner | 536/25.4 |

FOREIGN PATENT DOCUMENTS

| | | | |
|---|---|---|---|
| EP | 0 535 242 A1 | 3/1992 | C12Q/1/68 |
| EP | 0 649 852 A1 | 10/1994 | |
| EP | 0 668 361 A1 | 2/1995 | C12Q/1/68 |
| EP | 0 416 817 B1 | 10/1996 | |
| WO | WO 89/10977 | 11/1989 | |
| WO | WO 90/01564 | 2/1990 | C12Q/1/68 |

(List continued on next page.)

OTHER PUBLICATIONS

Brenner et al., "In vitro cloning of complex mixtures of DNA on microbeads: Physical separation of differentially expressed cDNAs," Proc Natl Acad Sci USA, Feb. 15, 2000, vol. 97, No. 4, pp. 1665–1670.

(List continued on next page.)

*Primary Examiner*—Ardin H. Marschel
(74) *Attorney, Agent, or Firm*—Morgan, Lewis & Bockius LLP

(57) ABSTRACT

Methods of selecting tag nucleic acids and VLSIPS™ arrays and the arrays made by the methods are used to label and track compositions, including cells and viruses, e.g., in libraries of cells or viruses. In addition to providing a way of tracking compositions in mixtures, the tags facilitate analysis of cell and viral phenotypes.

10 Claims, 7 Drawing Sheets

FOREIGN PATENT DOCUMENTS

| WO | WO 92/10092 | 11/1991 | |
|---|---|---|---|
| WO | WO 93/09668 | 5/1993 | ............ A01N/1/02 |
| WO | WO 94/11530 | 11/1993 | |
| WO | WO 95/11995 | 5/1995 | |
| WO | WO 95/21265 | 8/1995 | ............ C12Q/1/68 |
| WO | WO 96/27680 | 9/1996 | ............ C12Q/1/68 |
| WO | WO 97/31256 | 8/1997 | |
| WO | WO 97/45559 | 12/1997 | |
| WO | WO 98/03673 | 1/1998 | |
| WO | WO 99/35293 | 7/1999 | |
| WO | WO 00/20639 | 4/2000 | |
| WO | WO 00/26411 | 5/2000 | |

OTHER PUBLICATIONS

Brenner et al., "Gene expression analysis by massively parallel signature sequencing (MPSS) on microbead arrays," Nature Biotechnology, Jun. 2000. vol. 18, pp. 630–634.
Rychlik et al., Nucleic Acids Research, vol. 17, No. 21, pp. 8543–8551, 1989.*
Fodor, et al., (1991) Science, 251: 767–777.
Lipshutz, et al. (1995) BioTechniques 19(3): 442–447.
Fodor, et al. (1993) Nature 364: 555–556.
Medlin (1995) Environmental Health Perspectives 244–246.
Vesnaver, et al. (1989) Proc. Natl. Acad. Sci. USA 86, 3614–3618.
Wetmur, (1991) Critical Reviews in Biochemistry and Molecular Biology 26(3/4) 227–259.
Breslauer, et al. (1986) Proc. Natl. Acad. Sci. USA 83, 3746–3750.
Bugawan, et al. (1994) Tissue Antigens 44: 137–147.
Nizetic, et al. (1991) Proc. Natl. Acad. Sci. USA 88: 3233–3237.
Alderton, et al. (1994) Analytical Biochemistry 218: 98–102.
Bonaldo, et al. (1994) Human Molecular Genetics 3(9): 1663–1673.
Drmanac, et al. (1994) BioTechniques 17(2): 328–336.
Bains (1993) GATA 10(3–4): 84–94.
Drmanac, et al. Science (1993) 260: 1649–1652.
Madueno, et al., Genetics (1995) 139: 1631–1647.
Khrapko, et al. (1991) DNA Sequence—J. DNA Sequencing and Mapping 1: 375–388.
Hensel, et al. (1995) Science 269: 400–403.
Chetverin and Kramer (1994) Bio/Technology 12: 1093–1099.
Hensel et al, Simultaneous Identification of Bacterial Virulence Genes by Negative Selection, Jul. 21, 1995, vol. 269 pp. 400–403.
Barany, F., "Genetic disease detection and DNA amplification using cloned thermostable ligase" *Proc. Natl. Acad. Sci. USA* 88:189–193 (Jan. 1991).
Church, G.M. and Kieffer–Higgins, S., "Multiplex DNA sequencing" *Science 240*:185–188 (Apr. 8, 1988).
Luo, J. et al., "Improving the fidelity of *Thermus thermophilus* DNA ligase" *Nucl. Acids Res.* 24(14):3071–3078 (1996).
Wiedmann, M. et al., "Ligase Chain Reaction (LCR)—Overview and Applications" *PCR Meth. Appl. 3*(4):S51–S64 (Feb. 1994).
Southern et al., "Analyzing and comparing nucleic acid sequences by hybridization to arrays of oligonucleotides: Evaluation using experimental models" *Genomics* (1992) 13:1008–1017.
Elder, "Analysis of DNA Oligonucleotide Hybridization Data by Maximum Entropy" In "Maximum Entropy and Bayesian Methods" (eds. Mohammad–Djafari and Demoment) Kluwer, Dordrecht, 1992, pp. 363–371.
Pease et al., Light–generated oligonucleotide arrays for rapid DNA sequence analysis., *Proc. Natl. Acad. Sci.,* 91:5022–5026 (May 1994).
Fidanza J.A. et al., Oligonucleotide analog arrays for enhanced hybridization, *Abstracts of papers American Chemical Society* 213 (1–3) 1997. ORGN 303. issn: 0065-7727.

* cited by examiner

20mer ARRAY

HYBRIDIZED WITH CONTROL OLIGONUCLEOTIDE

PCR DELETION STRATEGY

FIG. 3

Up-stream 86mer
    UP-STREAM ADE 1 HOMOLOGY   TAG PRIMING SITE      20MER TAG      kan$^r$ homology
AAAGAATACACATACGAAATATTAACCATAGATGTCCACGAGGTCTCTTTGGTGCGCCCACAAACAAACTATAGTGAGTCGTAT Up-stream flanking 20mer
AAAGAATACACATACGAAAT Down-stream 66mer
DOWN-STREAM     ADE 1 HOMOLOGY            kan$^r$ homology
ATTCAGTGAGGAGTTACACTGGCGACTTGTAGTATATGTAAATCACGTTAAACAGCTATGACCATG Down-stream flanking 20mer
ATTCAGTGAGGAGTTACACT

FIG. 4

Transformation Results

| ORF | GeneBank | ORF size | Transformation efficiency | 20mer TAG (x,y) | SEQUENCE |
|---|---|---|---|---|---|
| ADE 1 | M61209 | 320aa | 100% (8/8) | (6,0) | tttggtgcgcccacaaacaa |
| ADE 2 | M59824 | 520aa | 50% (4/8) | (7,1) | ggctctcgacaaatctcaaa |
| ADE 3 | G7733 | 945aa | 50% (4/8) | (8,0) | gctgtctccaaagcacgaaa |
| ADE 4 | M74309 | 530aa | 100% (8/8) | (9,1) | gcgcttcgccaacagataaa |
| ADE 5 | X04337 | 802aa | 100% (8/8) | (10,0) | gcctgctgcaaaccattaaa |
| ARO A | X60190 | 377aa | 75% (6/8) | (11,1) | gggcgtccaacaatgcacaa |
| ARO 7 | M24517 | 256aa | 100% (8/8) | (12,0) | gccttcgcaacaatggacaa |
| TRP 2 | K01388 | 529aa | 100% (8/8) | (13,1) | cctctcagcaaatggtacaa |
| TRP 3 | K01386 | 485aa | 88% (7/8) | (14,0) | ggtctgctcaaatacaccaa |
| TRP 4 | X04273 | 380aa | 75% (6/8) | (15,1) | gcagatgccaaacggtccaa |
| TRP 5 | V01342 | 707aa | 88% (7/8) | (16,0) | gcccgaggcaaattcagcaa |

COMPLETE MEDIA

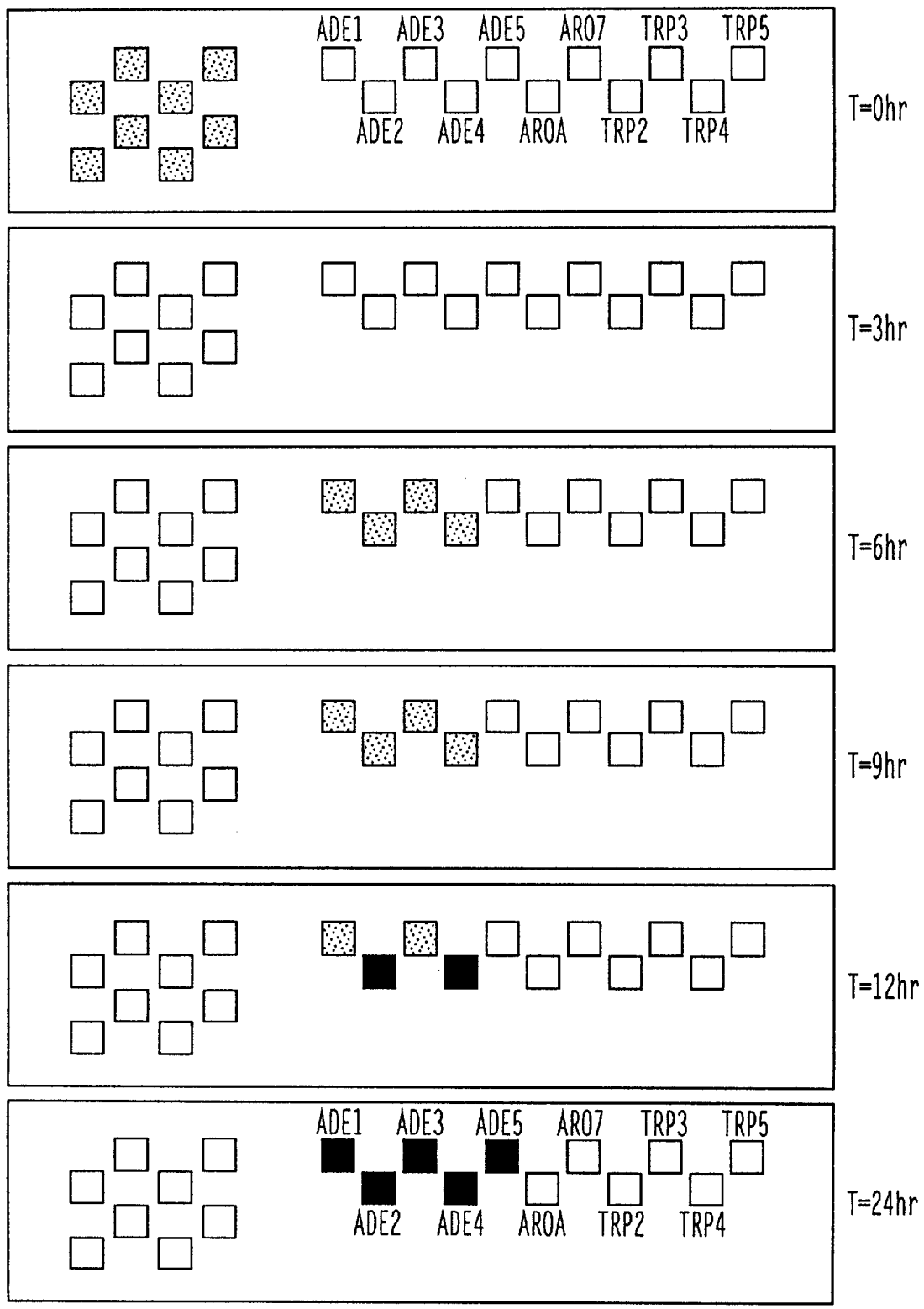

TRP DROP-OUT MEDIA

```
                          SEQUENCE LISTING (1) GENERAL INFORMATION:

(iii) NUMBER OF SEQUENCES: 56

(2) INFORMATION FOR SEQ ID NO:1:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

AAAGAATACA CATACGAAAT ATTAACGATA GATGTCCACG AGGTCTCTTT GGTGCGCCCA          60

CAAACAAACT ATAGTGAGTC GTAT                                                84

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

AAAGAATACA CATACGAAAT                                                     20

(2) INFORMATION FOR SEQ ID NO:3:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

ATTCAGTGAG GAGTTACACT GGCGACTTGT AGTATATGTA AATCACGTTA AACAGCTATG          60

ACCATG                                                                    66

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:
```

```
ATTCAGTGAG GAGTTACACT                                              20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

TTTGGTGCGC CCACAAACAA                                              20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GGCTCTCGAC AAATCTCAAA                                              20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GCTGTCTCCA AAGCACGAAA                                              20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GCGCTTCGCC AACAGATAAA                                              20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GCCTGCTGCA AACCATTAAA                                              20
```

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

GGGCGTCCAA CAATGCACAA                                              20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GCCTTCGCAA CAATGGACAA                                              20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

CCTCTCAGCA AATGGTACAA                                              20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GGTCTGCTCA AATACACCAA                                              20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

GCAGATGCCA AACGGTCCAA                                              20

(2) INFORMATION FOR SEQ ID NO:15:

(i) SEQUENCE CHARACTERISTICS:
        (A) LENGTH: 20 base pairs (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

GCCCGAGGCA AATTCAGCAA                            20

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

CCCTCACTCA CTCACTCA                              18

(2) INFORMATION FOR SEQ ID NO:17:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1
        (D) OTHER INFORMATION: /note= "N = preselected fixed
            nucleotide"

(ix) FEATURE:
        (A) NAME/KEY: -
        (B) LOCATION: 2
        (D) OTHER INFORMATION: /note= "N = preselected fixed
            nucleotide"

(ix) FEATURE:
        (A) NAME/KEY: -
        (B) LOCATION: 16
        (D) OTHER INFORMATION: /note= "N = preselected fixed
            nucleotide"

(xi) SEQUENCE DESCRIPTION: SEQ ID NO:17:

NNNNNNNNNN NNNATN                                16

(2) INFORMATION FOR SEQ ID NO:18:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

CCATGAATAG AAGATC                                16

(2) INFORMATION FOR SEQ ID NO:19:

(i) SEQUENCE CHARACTERISTICS:
        (A) LENGTH: 16 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:19:

AAACAATTCT AACAGG                                                    16

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

AAACAAACAC CCGCGTGGTT                                                20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

AAACAAAGAC CCGCCGGTGT                                                20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

AAACAAATAC CCGCCGTGGG                                                20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

AAACAACAAC CCGCGTGTGG                                                20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:24:

AAACAACCAA CCCGGTGTGG                                          20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

AAACAACGAA CCCGCTGGTG                                          20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

AAACAACTAA CCCGCTGTGG                                          20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

AAACAAGAAC CCGCCGTTGG                                          20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

AAACAAGCAA CCCGGCGTGT                                          20

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

AAACAAGGAA CCCGCCTGGT                                          20

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

AAACAAGTAA CCCGCCTTTG          20

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

AAACAATAAC CCGCGCTGGG          20

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

AAACAATCAA CCCGCTTGGG          20

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

AAACAATGAA CCCGCGTCGG          20

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

AAACAATTAA CCCGCGTTCG          20

(2) INFORMATION FOR SEQ ID NO:35:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:35:

AAACACAAAC CCGGCTGGTG                                               20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

AAACACACAA CCCGTGGTGG                                               20

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

AAACACAGAA CCCGCTTTGG                                               20

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

AAACACATAA CCCGGCGGTG                                               20

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

AAACACCAAA CCCGTTGTGG                                               20

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:40:

AAACACCCAA ACCGTTGTGG                                                    20

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

AAACACCGAA ACCCTGTGGG                                                    20

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

AAACACCTAA ACCCTTGTGG                                                    20

(2) INFORMATION FOR SEQ ID NO:43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:43:

AAACACGAAA CCCGGTCGGT                                                    20

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:44:

AAACACGCAA ACCCGGTGGT                                                    20

(2) INFORMATION FOR SEQ ID NO:45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:45:

AAACACGGAA ACCCTCGGTG                                                         20

(2) INFORMATION FOR SEQ ID NO:46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:46:

AAACACGTAA ACCCGTCGGT                                                         20

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:47:

AAACACTAAA CCCGTGCGGT                                                         20

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

AAACACTCAA ACCCTGGTGG                                                         20

(2) INFORMATION FOR SEQ ID NO:49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

AAACACTGAA ACCCGTCTGG                                                         20

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:50:

AAACACTTAA ACCCGTTCGG                                                         20

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:51:

AAACAGAAAC CCGCTCGGTG    20

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:52:

AAACAGACAA CCCGGCTTGG    20

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:53:

AAACAGAGAA CCCGGCCTTG    20

(2) INFORMATION FOR SEQ ID NO:54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:54:

AAACAGATAA CCCGCTCTTG    20

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:55:

AAACAGCAAA CCCGTGGCGT    20

(2) INFORMATION FOR SEQ ID NO:56:

(i) SEQUENCE CHARACTERISTICS:

```
    (A) LENGTH: 20 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:56:

AAACAGCCAA ACCGCGTGGT                                              20
```

SELECTING TAG NUCLEIC ACIDS

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

COMPUTER PROGRAM LISTING APPENDIX

The present specification includes a compact disc labeled "Copy 1" comprising a Computer Program Listing Appendix and an exact duplicate compact disc labeled "Copy 2." Said Computer Program Listing Appendix was created on May 23, 2002 and comprises text listings of the computer programs written in the "C" language "tags.ccp.txt" (11,505 bytes) and "tags895.ccp.txt" (10,895 bytes). The content of the Computer Program Listing Appendix is hereby incorporated by reference in its entirety.

FIELD OF THE INVENTION

This invention provides sets of nucleic acid tags, arrays of oligonucleotide probes, nucleic acid-tagged sets of recombinant cells and other compositions, and methods of selecting oligonucleotide probe arrays. The invention relates to the selection and interaction of nucleic acids, and nucleic acids immobilized on solid substrates, including related chemistry, biology, and medical diagnostic uses.

BACKGROUND OF THE INVENTION

Methods of forming large arrays of oligonucleotides and other polymers on a solid substrate are known. Pirrung et al., U.S. Pat. No. 5,143,854 (see also PCT Application No. WO 90/15070), McGall et al., U.S. Pat. No. 5,412,087, Chee et al. SN PCT/US94/12305, and Fodor et al., PCT Publication No. WO 92/10092 describe methods of forming arrays of oligonucleotides and other polymers using, for example, light-directed synthesis techniques.

In the Fodor et al. publication, methods are described for using computer-controlled systems to direct polymer array synthesis. Using the Fodor approach, one heterogenous array of polymers is converted, through simultaneous coupling at multiple reaction sites, into a different heterogenous array. See also, Fodor et al. (1991) *Science*, 251: 767–777; Lipshutz et al. (1995) *BioTechniques* 19(3): 442–447; Fodor et al. (1993) *Nature* 364: 555–556; and Medlin (1995) *Environmental Health Perspectives* 244–246. The arrays are typically placed on a solid surface with an area less than 1 inch$^2$, although much larger surfaces are optionally used.

Additional methods applicable to polymer synthesis on a substrate are described, e.g., in U.S. Pat. No. 5,384,261, incorporated herein by reference for all purposes. In the methods disclosed in these applications, reagents are delivered to the substrate by flowing or spotting polymer synthesis reagents on predefined regions of the solid substrate. In each instance, certain activated regions of the substrate are physically separated from other regions when the monomer solutions are delivered to the various reaction sites, e.g., by means of groves, wells and the like.

Procedures for synthesizing polymer arrays are referred to herein as very large scale immobilized polymer synthesis (VLSIPS™) procedures. Oligonucleotide VLSIPS™ arrays are useful, for instance, in a variety of procedures for monitoring test nucleic acids in a sample. In probe arrays with multiple probe sets, many distinct hybridization interactions can be monitored simultaneously. However, unwanted hybridization between probes, or between probes and other nucleic acids, can make analysis of multiple hybridizations problematic. This invention solves these and other problems.

SUMMARY OF THE INVENTION

With this invention it is now possible to label and detect many individual components present, inter alia, in molecular, cellular and viral libraries using a limited number of hybridization conditions. Components are labeled with specially selected nucleic acid tags, and the presence of individual tags is monitored by hybridization to a probe array (typically a VLSIPS™ array of oligonucleotide probes). Thus, the tag nucleic acids are labels for the individual components, and the probe array provides a label reader which permits simultaneous detection of a very large number of tag nucleic acids. This facilitates massive parallel analysis of all of the components in a mixture in a single assay.

For instance, as explained herein, all of the members of a cellular library can be tested for response to an environmental stimulus using a mixture of all of the members of the cellular library in a single assay. This is accomplished, e.g., by labeling each member of the cellular library, e.g., by cloning a nucleic acid tag into each cell type in the library, mixing each cell type in the library in an appropriate solution, and exposing part of the solution to the selected environmental stimulus. The distribution of nucleic acids in the library before and after the environmental stimulus is compared by hybridization of the nucleic acids to a VLSIPS™ array, allowing for detection of cells which are specifically affected by the environmental stimulus.

Accordingly, the present invention provides, inter alia, tag nucleic acids, sets of tag nucleic acids, methods of selecting tag nucleic acids, libraries of cells, viruses or the like containing tag nucleic acids, arrays of oligonucleotide probes, arrays of VLSIPS™ probes, methods of selecting arrays of oligonucleotide probes, methods of detecting tag nucleic acids with VLSIPS™ arrays and other features which will become clear upon further reading.

In one class of embodiments, the invention provides a method of selecting a set of tag nucleic acids designed for minimal cross hybridization to a VLSIPS™ array. The absence of cross hybridization facilitates analysis of hybridization patterns to VLSIPS™ arrays, because it reduces ambiguities in the interpretation of hybridization results which arise due to multiple nucleic acid species binding to a single species of probe on the VLSIPS™ array. Thus, in the selection methods of the invention, potential tags are excluded from set of tags where they bind to the same nucleic acid as selected tags under stringent conditions. The selection methods typically include the steps of selecting a specific thermal binding stability for the tag acids against complementary probes, and excluding tags which contain self-complementary regions. Often, the thermal binding stability of the tags is selected by specifying parameters which influence binding stability, such as the length and base composition (e.g., by selecting tags with the same AT to GC ratio of nucleotides) for the tag nucleic acids. In this regard, tags which form more GC bonds upon binding a complementary probe require fewer overall bases to have the same binding stability with a complementary probe as tags which have fewer GC residues. Binding stability is also affected by base stacking interactions, the formation of secondary structures and the choice of solvent in which a tag is bound to a probe.

The size of the tags can vary substantially, but is typically from about 8–150 nucleotides, more typically between 10 and 100 nucleotides, often between about 15 and 30 nucleotides, generally between about 15 and 25 nucleotides and, in one preferred embodiment, about 20 nucleotides in length. In a few applications, the tags are substantially longer than the probes to which they hybridize. The use of longer tags increases the number of tags from which non-cross hybridizing probes can be selected.

The tag nucleic acids are optionally selected to have constant and variable regions, which facilitates elimination of secondary structure arising from self-complementarity, and provides structural features for cloning and amplifying the tags. For instance, PCR binding sites or restriction enzyme sites are optionally incorporated into constant regions in the tags. In other embodiments, short constant regions are added in coding theory methods to prevent misalignment of the tags. Constant regions are optionally cleaved from the tag during processing steps, for instance by cleaving the tag nucleic acids with class II restriction enzymes.

Often it is desirable to eliminate tags which contain runs of 4 nucleotides selected from the group consisting of 4 X residues 4 Y residues and 4 Z residues, where X is selected from the group consisting of G and C, Y is selected from the group consisting of G and A, and Z is selected from the group consisting of A and T. The elimination of tags from a tag set which contain such runs of nucleotides reduces the formation of secondary structure in the selected tags in the tag set. In some embodiments, certain runs are permitted, while others are excluded. For instance, in one embodiment, runs of 4 A/T or G/C nucleotides are prohibited.

In many embodiments, tags which differ by fewer than about 80% of the total number of nucleotides which comprise the tags are excluded. For instance, all selected tags in a selected tag set preferably differ by at least about 4–5 nucleotides. It is also desirable to exclude tags which share substantial regions of sequence identity, because the regions of identity can cross-hybridize to nucleic acids which have subsequence complementary to the region of identity. For instance, where 20-mer tags are identical over regions of 9 or more nucleotides, they are typically excluded.

The tags in the tag sets of the invention typically differ by at least two nucleotides, and preferably by 3–5 nucleotides for a typical 20-mer. A list of tags which differ by at least two nucleotides can be generated by pairwise comparison of each tag, or by other methods. For instance, the tag sequences can be aligned for maximal correspondence and tags with a single-mismatch discarded. In one class of embodiments, the number of A+G nucleotides in each of the variable regions of each of the tags is selected to be even (or, alternatively, odd), providing a "parity base" or "error correcting base" which provides that each tag have at least two hybridization mismatches between every tag in the tag set, and any individual complementary nucleic acid probe (other than the probe which is a perfect complement to the tag). Other methods of ensuring that at least two mismatches exist between every tag in a tag set and any individual hybridization probe are also appropriate.

In general, the selection of the tag nucleic acids facilitates selection of the probe nucleic acids, e.g., on VLSIPS™ arrays used to monitor the tag nucleic acids by hybridization. Specifically, the probes on the array are selected for their ability to hybridize to variable sequences in the set of tag nucleic acids (the "variable" region of a tag which does not include a constant region is the entire tag). Thus, all of the rules for selection of tag nucleic acids can be applied to the selection of probe nucleic acids, for example by performing the tag selection steps and then determining the complementary set of probe nucleic acids.

In another class of embodiments, the invention provides compositions comprising sets of tag nucleic acids, which include a plurality of tag nucleic acids. In preferred embodiments, the set of tag nucleic acids comprises from 100–100,000 tags. Typically, a tag set will include between about 500 and 15,000 tags. Usually, the number of tags in a tag set is between about 5,000 and about 14,000 tags. In one preferred embodiment, a set of tags of the invention comprises about 8,000–9,000 tags. The tag sequences typically comprise a variable region, where the variable region for each tag nucleic acid in the set of tag nucleic acids has the same the same G+C to A+T ratio, approximately the same $T_m$, the same length and do not cross-hybridize to a single complementary probe nucleic acid. Most typically, the tag nucleic acids in the set of tag nucleic acids cannot be aligned with less than two differences between any two of the tag nucleic acids in the set of tag nucleic acids, and often at least 5 differences exist between any pair of tags in a tag set. In one embodiment, the tags also comprise a constant region such as a PCR primer binding site for amplification of the tag.

In one class of embodiments, the invention provides a method of labeling a composition, comprising associating a tag nucleic acid with the composition, wherein the tag nucleic acid is selected from a group of tag nucleic acids which do not cross-hybridize and which have a substantially similar $T_m$. Typically, the tag labels are detected with a VLSIPS™ array which comprises probes complementary to the tags used to label the composition.

As described herein, preferred compositions include constituents of cellular, viral or molecular libraries such as recombinant cells, recombinant viruses or polymers. However, one of skill will readily appreciate that other compositions can also be labeled using the nucleic acid tags of the invention, and the tags detected using VLSIPS™ arrays. For instance, high denomination currency can be labeled with a set of nucleic acid tags, and counterfeits detected by monitoring hybridization of a wash of the currency (or, e.g., a PCR amplification of attached nucleic acids which encode tag sequences) with an appropriate VLSIPS™ array.

In another class of embodiments, the invention provides methods of pre-selecting experimental probes in an oligonucleotide probe array, wherein the probes have substantially uniform hybridization properties and do not cross hybridize to a target tag nucleic acid. In the methods, a ratio of G+C to A+T nucleotides shared by the experimental probes in the array is selected and all possible 4 nucleotide subsequences for the probes of the array are determined. All potential probes from the array which contain prohibited 4 nucleotide sub-sequences are excluded from the experimental probes of the array. 4 nucleotide subsequences are prohibited when the nucleotide subsequences are selected from the group consisting of self-complementary probes, $A_4$ probes, $T_4$ probes, and $[G,C]_4$ probes. Also, where the target tag nucleic acid comprises a constant region, all probes complementary to the constant region sub-sequence of the target tag nucleic acid are prohibited, and not present in the tag set. Typically, a length for the probes in the array is selected, although non-hybridizing portions of the probe (i.e., nucleotides which do not hybridize to a target nucleic acid) optionally vary between different classes of probes. "Experimental probes" hybridize to a target tag nucleic acid, while "control" probes either do not hybridize to a target tag nucleic acid, or bind to a nucleic acid which has hybridization properties which differ from those of the target tag nucleic acids in a tag nucleic acid set. For instance, control probes are optionally used in VLSIPS™ arrays to check hybridization stringency against a known nucleic acid.

In one class of methods of the invention, a plurality of test nucleic acids are simultaneously detected in a sample. In the methods, an array of experimental probes which do not cross hybridize to a target under stringent conditions is used to detect the target nucleic acids. Typically, the ratio of G+C bases in each experimental probe is substantially identical. The probes of the array are arranged into probe sets in which each probe set comprises a homogeneous population of oligonucleotide probes. For example, many individual probes with the same nucleotide sequence are arranged in proximity to one another on the surface of an array to form a particular geometric shape. Probe sets are arranged in proximity to each other to form an array of probes. For instance, where the probe array is a VLSIPS™ array, the probe sets are optionally arranged into squares on the surface of a substrate, forming a checkerboard pattern of probe sets on the substrate.

The probes of the array specifically hybridize to at least one test nucleic acid in the sample under stringent hybridization conditions. The method further comprises detecting hybridization of the test nucleic acids to the array of oligonucleotide probes. Typically, the test nucleic acids comprise tag sequences, which bind to the experimental probes of the array.

In one class of embodiments, the invention provides an array of oligonucleotide probes comprising a plurality of experimental oligonucleotide probe sets attached to a solid substrate, wherein each experimental oligonucleotide probe set in the array hybridizes to a different target nucleic acid under stringent hybridization conditions. Each experimental oligonucleotide probe in the probe sets of the array comprises a constant region and a variable region. The variable region does not cross hybridize with the constant region under stringent hybridization conditions, and the nucleic acid probes do not cross-hybridize to target nucleic acids. Typically, the probes from each probe set differ from the probes of every other probe set in the array by the arrangement of at least two nucleotides in the probes of the probe set. Generally, the ratio of G+C bases in each probe for each experimental probe set is substantially identical (meaning that the G+C ratio does not vary by more than 5%), thereby assuring that they hybridize to a target with similar avidity under similar hybridization conditions. The arrays optionally comprise control probes, e.g., to assess hybridization conditions by monitoring binding of a known quantitated nucleic acid to the control probe.

In another class of embodiments, the invention provides a plurality of recombinant cells or recombinant viruses comprising tag nucleic acids, which tag nucleic acids comprise a constant region and a variable region. Typically, the variable region for each tag nucleic acid in the set of tag nucleic acids has approximately the same $T_m$, (e.g., the same G+C to A+T ratio and the same length) and does not cross-hybridize to a probe nucleic acid. Different tag nucleic acids in the set of tag nucleic acids found in the different recombinant cells cannot be aligned with less than two differences between the tag nucleic acids. Generally, the recombinant cells are selected from a library of genetically distinct recombinant cells (eukaryotic, prokaryotic or archaebacterial) or viruses. For example, in one class of preferred embodiments, the cells are yeast cells. In another class of preferred embodiments, the cells are of mammalian origin.

The present invention provides arrays of oligonucleotides attached to solid substrates. Typically, the oligonucleotide probes in the array are arranged into probe sets at defined locations in the array to enhance signal processing of hybridization reactions between the oligonucleotide probes and test nucleic acids in a sample. The oligonucleotide arrays can have virtually any number of different oligonucleotide sets, determined largely by the number or variety of test nucleic acids or nucleic acid tags to be screened against the array in a given application. In one group of embodiments, the array has from 10 up to 100 oligonucleotide sets. In other groups of embodiments, the arrays have between 100 and 10,000 sets. In certain embodiments, the arrays have between 10,000 and 100,000 sets, and in yet other embodiments the arrays have between 100,000 and 1,000,000 sets. Most preferred embodiments will have between 7,500 and 12,500 sets. For example in one preferred embodiment, the arrays will comprise about 8,000 sets of oligonucleotide probes. In preferred embodiments, the array will have a density of more than 100 sets of oligonucleotides at known locations per $cm^2$, or more preferably, more than 1000 sets per $cm^2$. In some embodiments, the arrays have a density of more than 10,000 sets per $cm^2$.

The present invention also provides kits embodying the inventive concepts outlined above. For example, kits of the invention comprise any of the arrays, cells, libraries or tag sets described herein. Also, because the methods of using the arrays and tags optionally include PCR, LCR and other in vitro amplification techniques for amplifying tag nucleic acids, the kits of the invention optionally include reagents for practicing in vitro amplification methods such as taq polymerase, nucleotides, computer software with tag selection programs and the like. The kits also optionally comprise nucleic acid labeling reagents, instructions, containers and other items that will be apparent to one of skill upon further reading.

BRIEF DESCRIPTION OF THE DRAWING

FIG. 3 shows oligonucleotides used to generate the ADE1 tagged deletion strain. Similar sets of oligonucleotides were synthesized for the other ten auxotrophic ORFS FIG. 4 shows transformation results and tag information for eleven auxotrophic ORFS. Eight colonies from each transformation were analyzed by replica plating and PCR the resulting targeting efficiency is shown for each of the ORFS. The sequence and (SEQ ID No: 5–15) x,y coordinates are shown for the molecular tags that were used to uniquely label the different deletion strains.

DEFINITIONS

Figure 1:
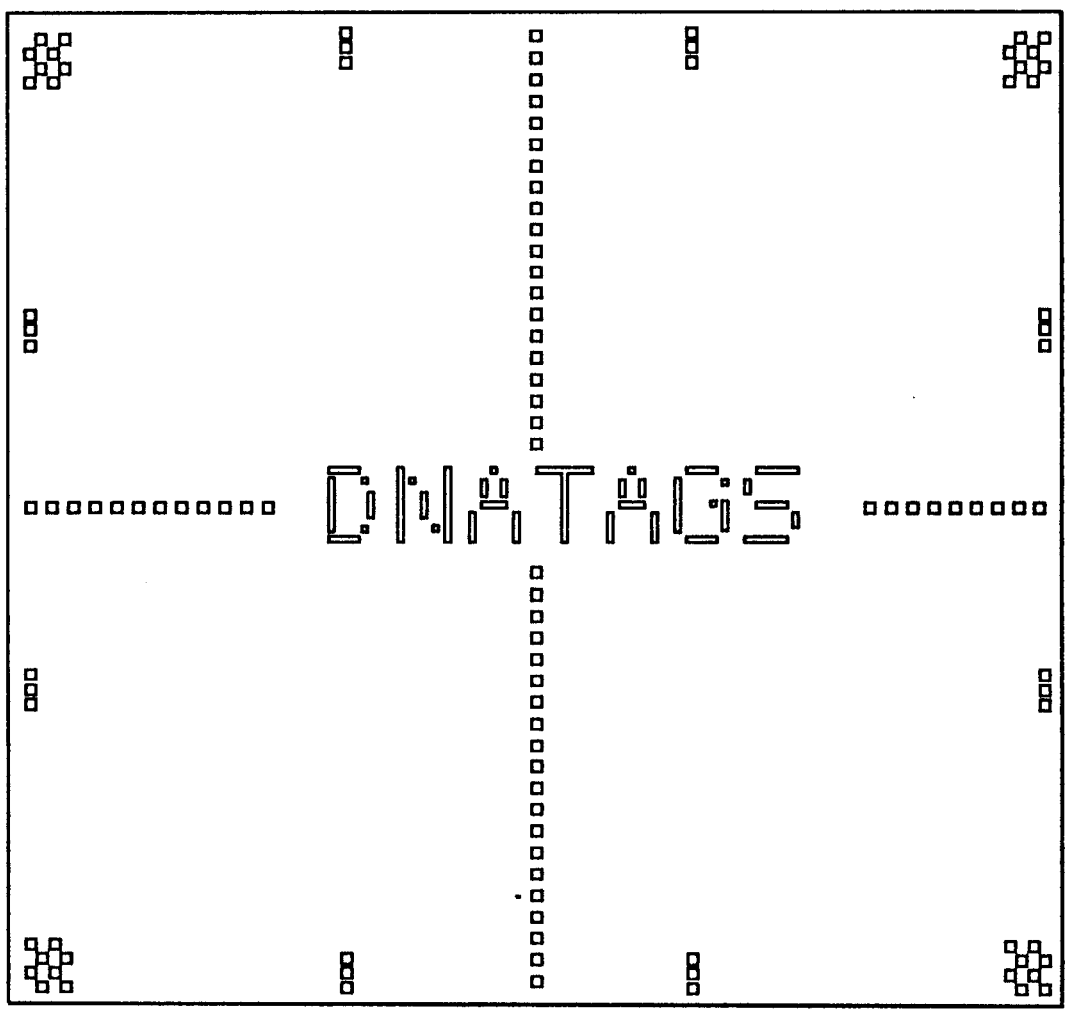
FIG. 1 is a depiction of an actual scanned image of a 1.28 cm by 1.28 cm high-density array hybridized with a fluorescently labeled control oligonucleotide. The array contains complementary sequences to 4,500 20mer tags selected as described in Table 1. White boxes (□) within the array represent positive binding of a control oligonucleotide to the sequence at that position in the array. Control oligonucleotides are synthesized in the corners and in a cross-hair pattern across the array to verify the uniformity of the synthesis and the hybridization conditions. "DNA TAGS" was spelled out with control oligonucleotides as well. The dark areas indicate the location of the 4,500 20 base molecular tags. Note that there is no cross-hybridization of the control oligonucleotide and the molecular tag sequences.

Unless defined otherwise, technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York) and March (March, *Advanced Organic Chemistry Reactions, Mechanisms and Structure* 4th ed J. Wiley and Sons (New York, 1992) provides one of skill with a general guide to many of the terms used in this invention.

Although one of skill will recognize many methods and materials similar or equivalent to those described herein which can be used in the practice of the present invention, the preferred methods and materials are described. For purposes of the present invention, the following terms are defined below.

"Eukaryotic" cells are cells which contain at least one nucleus in which the cell's genomic DNA is organized, or which are the differentiated offspring of cells which contained at least one nucleus. Eukaryotes are distinguished from prokaryotes which are cellular organisms which carry their genomic DNA in the cell's cytoplasm.

A "nucleoside" is a pentose glycoside in which the aglycone is a heterocyclic base; upon the addition of a phosphate group the compound becomes a nucleotide. The major biological nucleosides are β-glycoside derivatives of D-ribose or D-2-deoxyribose. Nucleotides are phosphate esters of nucleosides which are acidic due to the hydroxy groups on the phosphate. The polymerized nucleotides deoxyribonucleic acid (DNA) and ribonucleic acid (RNA) store the genetic information which controls all aspects of an organism's interaction with its environment. The nucleosides of DNA and RNA are connected together via phosphate units attached to the 3 position of one pentose and the 5 position of the next pentose.

A "nucleic acid" is a deoxyribonucleotide or ribonucleotide polymer in either single- or double-stranded form, and unless otherwise limited, encompasses known analogs of natural nucleotides that function in a manner similar to naturally occurring nucleotides.

An "oligonucleotide" is a nucleic acid polymer composed of two or more nucleotides or nucleotide analogues. An oligonucleotide can be derived from natural sources but is often synthesized chemically. It is of any size.

An "oligonucleotide array" is a spatially defined pattern of oligonucleotide probes on a solid support. A "preselected array of oligonucleotides" is an array of spatially defined oligonucleotides on a solid support which is designed before being constructed (i.e., the arrangement of polymers on solid substrate during synthesis is deliberate, and not random).

A "nucleic acid reagent" utilized in standard automated oligonucleotide synthesis typically caries a protected phosphate on the 3' hydroxyl of the ribose. Thus, nucleic acid reagents are referred to as nucleotides, nucleotide reagents, nucleoside reagents, nucleoside phosphates, nucleoside-3'-phosphates, nucleoside phosphoramidites, phosphoramidites, nucleoside phosphonates, phosphonates and the like. It is generally understood that nucleotide reagents carry a protected phosphate group in order to form a phosphodiester linkage.

A "protecting group" as used herein, refers to any of the groups which are designed to block one reactive site in a molecule while a chemical reaction is carried out at another reactive site. More particularly, the protecting groups used herein can be any of those groups described in Greene, et al., *Protective Groups In Organic Chemistry*, 2nd Ed., John Wiley & Sons, New York, N.Y., 1991, which is incorporated herein by reference. The proper selection of protecting groups for a particular synthesis is governed by the overall methods employed in the synthesis. For example, in "light-directed" synthesis, discussed herein, the protecting groups are typically photolabile protecting groups such as NVOC, MeNPoc, and those disclosed in co-pending Application PCT/US93/10162 (filed Oct. 22, 1993), incorporated herein by reference. In other methods, protecting groups are removed by chemical methods and include groups such as FMOC, DMT and others known to those of skill in the art.

A "solid substrate" has a fixed organizational support matrix, such as silica, polymeric materials, or glass. In some embodiments, at least one surface of the substrate is partially planar. In other embodiments it is desirable to physically separate regions of the substrate to delineate synthetic regions, for example with trenches, grooves, wells or the like. Example of solid substrates include slides, beads and polymeric chips. A solid support is "functionalized" to permit the coupling of monomers used in polymer synthesis. For example, a solid support is optionally coupled to a nucleoside monomer through a covalent linkage to the 3'-carbon on a furanose. Solid support materials typically are unreactive during polymer synthesis, providing a substratum to anchor the growing polymer. Solid support materials include, but are not limited to, glass, silica, controlled pore glass (CPG), polystyrene, polystyrene/latex, and carboxyl modified Teflon. The solid substrates are biological, nonbiological, organic, inorganic, or a combination of any of these, existing as particles, strands, precipitates, gels, sheets, tubing, spheres, containers, capillaries, pads, slices, films, plates, slides, etc. depending upon the particular application. In light-directed synthetic techniques, the solid substrate is often planar but optionally takes on alternative surface configurations. For example, the solid substrate optionally contains raised or depressed regions on which synthesis takes place. In some embodiments, the solid substrate is chosen to provide appropriate light-absorbing characteristics. For example, the substrate may be a polymerized Langmuir Blodgett film, functionalized glass, Si, Ge, GaAs, GaP, $SiO_2$, $SiN_4$, modified silicon, or any one of a variety of gels or polymers such as (poly)tetrafluoroethylene, (poly) vinylidendifluoride, polystyrene, polycarbonate, or combinations thereof. Other suitable solid substrate materials will be readily apparent to those of skill in the art. Preferably, the surface of the solid substrate will contain reactive groups, such as carboxyl, amino, hydroxyl, thiol, or the like. More preferably, the surface is optically transparent and has surface Si—OH functionalities, such as are found on silica surfaces A substrate is a material having a rigid or semi-rigid surface. In spotting or flowing VLSIPS™ techniques, at least one surface of the solid substrate is optionally planar, although in many embodiments it is desirable to physically separate synthesis regions for different polymers with, for example, wells, raised regions, etched trenches, or the like. In some embodiments, the substrate itself contains wells, trenches, flow through regions, etc. which form all or part of the regions upon which polymer synthesis occurs.

The term "recombinant" when used with reference to a cell or virus indicates that the cell or virus encodes a DNA or RNA whose origin is exogenous to the cell or virus. Thus, for example, recombinant cells optionally express nucleic acids (e.g., RNA) not found within the native (non-recombinant) form of the cell.

"Stringent" hybridization conditions are sequence dependent and will be different with different environmental parameters (salt concentrations, presence of organics etc.). Generally, stringent conditions are selected to be about 5° C. to 20° C. lower than the thermal melting point ($T_m$) for the specific nucleic acid sequence at a defined ionic strength and pH. Preferably, stringent conditions are about 5° C. to 10° C. lower than the thermal melting point for a specific nucleic acid bound to a complementary nucleic acid. The $T_m$ is the temperature (under defined ionic strength and pH) at which 50% of a nucleic acid (e.g., tag nucleic acid) hybridizes to a perfectly matched probe. "Thermal binding stability" is a measure of the temperature-dependent stability of a nucleic acid duplex in solution. The thermal binding stability for a duplex is dependent on the solvent, base composition of the duplex, number and type of base pairs, position of base pairs in the duplex. length of the duplex and the like.

"Stringent" wash conditions are ordinarily determined empirically for hybridization of each set of tags to a corresponding probe array. The arrays are first hybridized (typically under stringent hybridization conditions) and then washed with buffers containing successively lower concentrations of salts, and/or higher concentrations of detergents, and/or at increasing temperatures until the signal to noise ratio for specific to non-specific hybridization is high enough to facilitate detection of specific hybridization.

Stringent temperature conditions will usually include temperatures in excess of about 30° C., more usually in excess of about 37° C., and occasionally in excess of about 45° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is more important than the measure of any single parameter. See, e.g., Wetmur and Davidson (1968) *J. Mol. Biol.* 31:349–370 and Wetmur (1991) *Critical Reviews in Biochemistry and Molecular Biology* 26(3/4), 227–259.

The term "identical" in the context of two nucleic acid sequences refers to the residues in the two sequences which are the same when aligned for maximum correspondence. Optimal alignment of sequences for comparison can be conducted, e.g., by the local homology algorithm of Smith and Waterman *Adv. Appl. Math.* 2: 482 (1981), by the homology alignment algorithm of Needleman and Wunsch *J. Mol. Biol* 48:443 (1970), by the search for similarity method of Pearson and Lipman *Proc. Natl. Acad. Sci.* (*U.S.A.*) 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

A nucleic acid "tag" is a selected nucleic acid with a specified nucleic acid sequence. A nucleic acid "probe" hybridizes to a nucleic acid "tag." In one typical configuration, nucleic acid tags are incorporated as labels into biological libraries, and the tag nucleic acids are detected using a VLSIPS™ array of probes. Thus, the "tag" nucleic acid functions in a manner analogous to a bar code label, and the VLSIPS™ array of probes functions in a manner analogous to as a bar code label reader. A "list of tag nucleic acids" is a pool of tag nucleic acids, or a representation (i.e., an electronic or paper copy) of the sequences in the pool of tag nucleic acids. The pool of tags can be, for instance, all possible tags of a specified length (i.e., all 20-mers), or a subset thereof.

A set of nucleic acid tags binds to a probe with "minimal cross hybridization" when a single species (or "type") of tag in the tag set accounts for the majority of all tags which bind to an array comprising a probe species under stringent conditions. Typically, about 80% or more of the tags bound to the probe species are of a single species under stringent conditions. Usually about 90% or more of the tags bound to the probe species are of a single species under stringent conditions. Preferably 95% or more of the tags bound to the probe species are of a single species under stringent conditions.

DETAILED DESCRIPTION OF THE INVENTION

The invention provides methods of selecting and detecting sets of tag nucleic acids. In addition, the invention provides arrays of probe nucleic acids for detecting tag nucleic acids, sets of tag nucleic acids and cells which comprise tag nucleic acids. The tag nucleic acids, probe nucleic acid arrays and cells transformed with tag nucleic acids have a variety of uses. Most commonly, the tag nucleic acids of the invention are used to tag cells with known genotypic markers (mutants, polymorphisms, etc.), and to track the effect of environmental changes on the viability of tagged cells.

For instance, with the completion of the sequencing of S. cerevisiae, thousands of open reading frames (ORFs) have been identified. One strategy for identifying the function of the identified ORFs is to create deletion mutants for each ORF, followed by analysis of the resulting deletion mutants under a wide variety of selective conditions. Typically, the goal of such an analysis is to identify a phenotype that reveals the function of the missing ORF. If the analysis were to be carried out for each deletion mutant in a separate experiment, the required time and cost for monitoring the effect of altering an environmental parameter on each deletion mutant would be prohibitive. For instance, to identify ORFs which are required for synthesis of an amino acid, all of the thousands of ORF deletion mutants would be individually tested for the ability of the mutant to grow in media lacking the amino acid. Even if the analysis were carried out in a parallel fashion using, e.g., 96-well plates, the effort required to plate, organize, label and track each clone would be prohibitive. The present invention provides a much more cost-effective approach to screening cells.

In the methods of the invention, all of the thousands of deletion mutants described above can be tested in parallel in a single experiment. The deletion mutants are each tagged with a tag nucleic acid, and the deletion mutants are then pooled. The pooled, tagged deletion mutants are then simultaneously tested for their response to an environmental stimulus (e.g., growth in medium lacking an amino acid). The deletion cell-specific tags are then read using a probe array such as a VLSIPS™ array. Thus, by analogy, the deletion cell-specific nucleic acid tags act as bar code labels for the cells and the VLSIPS™ array acts as a bar code reader.

While the example above specifically discusses labeling yeast cells, one of skill will appreciate that essentially any cell type can be labeled with the nucleic acid tags of the invention, including prokaryotes, eukaryotes, and archaebacteria. Also, essentially any virus can be similarly labeled, as can cellular organelles with nucleic acids (mitochondria, chloroplasts,. etc.). In fact, labeling by tag nucleic acids and detection by probe arrays is not in any way limited to biological materials. One of skill will recognize that many other compositions can also be labeled by nucleic acid tags and detected with probe arrays. Essentially anything which benefits from the attachment of a label can be labeled and detected by the tags, arrays, and methods of the invention.

For instance, high denominational currency, original works of art, valuable stamps, significant legal documents such as wills, deeds of property, and contracts can all be labeled with nucleic acid tags and the tags read using the probe arrays of the invention. Methods of attaching and cleaving nucleic acids to and from many substrates are well known in the art, including glass, polymers, paper, ceramics and the like, and these techniques are applicable to the nucleic acid tags of the invention.

One of skill will also appreciate that while many of the examples herein describe the use of a single tag nucleic acid to label a cell, multiple tags can also be used to label any cell, e.g., by cloning multiple nucleic acid tags into the cell. Similarly, multiple nucleic acid tags can be used to label a substance such as those described above. Indeed, multiple labels are typically preferred where the object of the nucleic acid tags is to detect forgery. For instance, the nucleic acids of the invention can be used to label a high denomination currency bill with hundreds, or even thousands, of distinct tags, such that visualization of the hybridization pattern of the tags on a VLSIPS™ array provides verification that the currency bill is genuine.

In certain embodiments, multiple probes bind to unique regions on a single tag. In these embodiments, the probes are typically relatively large, e.g., about 50 nucleotides or longer. Probes are selected such that each probe binds to a single region on a single tag. The use of tags which bind multiple probes increases the informational content of hybridization reactions by providing making it possible to monitor multiple hybridization events simultaneously.

One of skill will also appreciate that it is not necessary to hybridize a tag directly to a probe array to achieve essentially the same effect. For instance, tag nucleic acids are optionally (and preferably) amplified, e.g., using PCR or LCR or other known amplification techniques, and the amplification products ("amplicons") hybridized to the array. For instance, a nucleic acid tag optionally includes or is in proximity to PCR primer binding sites which, when amplified using standard PCR techniques, amplifies the tag nucleic acid, or a subsequence thereof. Thus, cells, or other tagged items can be detected even if the tag nucleic acids are present in very small quantities. One of skill will appreciate that a single molecule of a nucleic acid tag can easily be detected after amplification, e.g., by PCR. The complexity reduction from amplifying a selected mixture of tags (i.e., there are relatively few amplicon nucleic acid species as compared to a pool of genomic DNA) facilitates analysis of the mixture of tags.

In one preferred embodiment, tags are selected such that each selected tag has a complementary selected tag. For example, if a tag is cloned into an organism, the tag can be amplified using LCR, PCR or other amplification methods. The amplified tag is often double-stranded. In preferred embodiments, tag sets which include complementary sets of tags have corresponding probes for each complementary tag. Both strands of a double-stranded tag amplification product are separately monitored by the probe array. Hybridization of each of the strands of the double-stranded tag provides an independent readout for the presence or absence of the tag nucleic acid in a sample.

Selection of Tag Nucleic Acids.

This invention provides ways of selecting nucleic acid tag sets useful for labeling cells and other compositions as described above. The tag sets provided by the selection methods of the invention have uniform hybridization characteristics (i.e., similar thermal binding stability to complementary nucleic acids), making the tag sets suitable for detection by VLSIPS™ and other probe arrays, such as Southern or northern blots. Because the hybridization characteristics of the tags are uniform, all of the tags in the set are typically detectable using a single set of hybridization and wash conditions. As described in the Examples below, various selection methods of the invention were used to generate lists of about 10,000 suitable 20-mer nucleic acid tags from all of possible 20-mer sequences (about 1,200,000,000,000). The synthesis of a single array with 10,000 probes complementary to the 10,000 tag nucleic acids (i.e., for the detection of the tags) was carried out using standard VLSIPS™ techniques to make a VLSIPS™ array.

Desirable nucleic acid tag sets have several properties. These include, inter alia, that the hybridization of the tags to their complementary probe (i.e., in the VLSIPS™ array) is strong and uniform; that individual tags hybridize only to their complementary probes, and do not significantly cross hybridize with probes complementary to other sequence tags; that if there are constant regions associated with the tags (e.g., cloning sites, or PCR primer binding sites) that the constant regions do not hybridize to a corresponding probe set. If the selected tag set has the described properties, any mixture of tags can be hybridized to a corresponding array, and the absence or presence of the tag can be unambiguously determined and quantitated. Another advantage to such a tag set is that the amount of binding of any tag set can be quantitated, providing an indication of the relative ratio of any particular tag nucleic acid to any other tag nucleic acid in the tag set.

The properties outlined above are obtained by following some or all of the selection steps outlined below for selection of tag sequence characteristics.

(1) Determine all possible nucleic acid tags of a selected length, or with selected hybridization properties. Although the examples below provide ways of selecting tags from pools of tags of a single length for illustrative purposes, one of skill will appreciate that the tags can have different lengths, e.g., where the tags have the same (or closely similar) melting temperatures against perfectly complementary targets. One of skill will also appreciate that a subset of all possible tags can be used, depending on the application. For instance, where tags are used to detect an organism, 20 mers which either occur in the organism's genome, or do not occur in the organism's genome can be used as a starting point for a pool of potential nucleic acid tags. For instance, the entire genome of *S. cerevisiae* is available. In certain embodiments, endogenous sequences (e.g., those which appear in ORFs) can be used as tags, obviating the need for cloning tags into the organism. Thus, all possible 20-mers from the genome are determined from the genomic sequence, and 20-mers with desired hybridization characteristics to probes are selected. Alternatively, where tags are cloned into the organism, it is occasionally preferable to eliminate all 20-mers which appear naturally in the genome from consideration as tag sequences, so that introduced tag sequences are not confused with endogenous sequences in hybridization assays.

The selection of the length of the nucleic acid tag is dependent on the desired hybridization and discrimination properties of the probe array for detecting the tag. In general, the longer the tag, the higher the stringency of the hybridization and washes of the hybridized nucleic acids on the array. However, longer tags are not as easily discriminated on the array, because a single mismatch on a long nucleic acid duplex has less of a destabilizing effect on hybridization than a single mismatch on a short nucleic acid duplex. It is expected that one of skill is thoroughly familiar with the theory and practice of nucleic acid hybridization to an array of nucleic acids. In addition to the patents and literature cited supra in regards to the synthesis of VLSIPS™ arrays, Gait, ed. *Oligonucleotide Synthesis: A Practical Approach,* IRL Press, Oxford (1984); W. H. A. Kuijpers *Nucleic Acids Research* 18(17), 5197 (1994); K. L. Dueholm *J. Org. Chem.* 59, 5767–5773 (1994); S. Agrawal (ed.) *Methods in Molecular Biology,* volume 20; and Tissen (1993) *Laboratory Techniques in biochemistry and molecular biology—hybridization with nucleic acid probes, e.g.,* part I chapter 2 "overview of principles of hybridization and the strategy of nucleic acid probe assays", Elsevier, N.Y. provide a basic guide to nucleic acid hybridization.

Most typically, tags are between 8 and 100 nucleotides in length, and preferably between about 10 and 30 nucleotides in length. Most preferably, the tags are between 15 and 25 nucleic acids in length. For example, in one preferred embodiment, the nucleic acid tags are about 20 nucleotides in length.

(2) The tags are selected so that there is no complementarity between any of the probes in an array selected to hybridize to the tag set and any constant tag region (constant tag regions are optionally provided to provide primer binding sites, e.g. for PCR amplification of the remainder of the tag, or to limit the selected tags as described below). In other words, the complementary nucleic acid of the variable region of a nucleic acid tag cannot hybridize to any constant region of the nucleic acid tag. One of skill will appreciate that constant regions in tag sequences are optional, typically being used where a PCR or other primer binding site is used within the tag.

(3) The tags are selected so that no tag hybridizes to a probe with only one sequence mismatch (all tags differ by at least two nucleotides). Optionally, tags can be selected which have at least 2 mismatches, 3 mismatches, 4 mismatches 5 mismatches or more to a probe which is not perfectly complementary to the tag, depending on the application. Typically, all tag sequences are selected to hybridize only to a perfectly complementary probe, and the nearest mismatch hybridization possibility has at least two hybridization mismatches. Thus, the tag sequences typically differ by at least two nucleotides when aligned for maximal correspondence. Preferably, the tags differ by about 5 nucleotides when aligned for maximal correspondence (e.g., where the tags are 20-mers).

The tags are often selected so that they do not have identical runs of nucleotides of a specified length. For instance, where the tags are 20-mers, the tags are preferably selected so that no two tags have runs of about 9 or more nucleotides in common. One of skill will appreciate that the length of prohibited identity varies depending on the selected length of the tag. It was empirically determined that cross-hybridization occurs in tag sets when 20-mer tags have more than about 8 contiguous nucleotides in common.

(4) The tags are selected so that there is no secondary structure within the complementary probes used to detect the tags which are complementary to the tags. Typically, this is done by eliminating tags from a selected tag set which have subsequences of 4 or more nucleotides which are complementary.

(5) The tags are selected so that no secondary structure forms between a tag and any associated constant sequence. Self-complementary tags have poor hybridization properties in arrays, because the complementary portions of the probes (and corresponding tags) self hybridize (i.e., form hairpin structures).

(6) The tags are selected so that probes complementary to the tags do not hybridize to each other, thereby preventing duplex formation of the tags in solution.

(7) If there is more than one constant region in the tag, the constant regions of the tag are selected so that they do not self-hybridize or form hairpin structures.

(8) Where the tags are of a single length, the tags are selected so that they have roughly the same, and preferably exactly the same overall base composition (i.e., the same A+T to G+C ratio of nucleic acids). Where the tags are of differing lengths, the A+T to G+C ratio is determined by selecting a thermal melting temperature for the tags, and selecting an A+T to G+C ratio and probe length for each tag which has the selected thermal melting temperature.

One of skill will recognize that there are a variety of possible ways of performing the above selection steps. Most typically, selection steps are performed using simple computer programs to perform the selection in each of the steps outlined above; however, all of the steps are optionally performed manually. The following strategies are provided for exemplary purposes; one of skill will recognize that a variety of similar strategies can be used to achieve similar results.

In one embodiment, secondary structure was prevented within the tag, and hybridization within or between pairs of complementary probes (goals 4, 5, and 6 above) was prevented by analyzing 4 base subsequences within the tags which were dynamically excluded when any of the following properties were met:

(a) all tags with complementary regions of 4 or more bases, including those which overlap in sequence, and 4 mers which are self complementary. To prevent tag variable sequences from hybridizing to the constant primer sequences, regions of 4 or more bases in a tag which are complementary to 4 base sequences fully or partially contained in the constant sequence which were separated by at least 3 bases (i.e., the minimal separation typically required for hairpin formation) were prohibited.

(b) To assure uniformity of hybridization strength, runs of 4 mers comprised only of 4 As, 4 Ts or 4 G or C residues were prohibited. Excluding runs of T/A and G/A is also desirable.

Further selection is optionally performed to refine aspects of the selection steps outlined above. For instance, to select tags which are less likely to cross-hybridize, more fixed or restricted bases can be added for alignment purposes, the tags can be lengthened, and additional coding requirements can be imposed. In one embodiment, the tags selected by the method above is performed, and a subset of tags with reduced hybridization is selected. For example, a first tag from the set generated above is selected, and a second tag is selected from the tag set. If the second tag does not cross-hybridize with the first tag the second tag remains in the tag set. If it does cross-hybridize, the tag is discarded. Thus, each tag from the group selected by the methods outlined above is compared to every other tag in the group, and selected or discarded based upon comparison of hybridization properties. This process of comparison of one tag to every other possible tag in a pool of tags is referred to as pairwise comparison. Similar to the steps outlined above, cross-hybridization can be determined in a dynamic programming method as used for the sequence alignment above.

Refinement of the above methods include accounting for the differences in destabilization caused by positional effects of mismatches in the probe:tag duplex. The total number of mismatches is not the best estimate of hybridization potential because the amount of destabilization is highly dependent on both the positions and the types of the mismatches; for example, two adjacent mismatched bases in a 20 nucleotide duplex is generally less destabilizing than two mismatches spread at equal intervals. A better estimate of cross-hybridization potential can be obtained by comparing the two tags directly using dynamic programming or other methods. In these embodiments, a set of tag sequences obeying the following rules (in which the presence of a constant region in the tags is optional) is generated:

(A) All tags are the same length, N and have similar base composition. Certain runs of bases and potential hairpin structures are prohibited (see above).

(B) No two tag sequences contain an identical subsequence of length n, for some threshold length n. The second rule allows fast screening of the majority of cross-hybridizing probes (the selection method is linear), leaving a short list for which each pair of probes is compared for similarity (this takes time proportional to the square of the number of probes). The method is essentially an alphabetical tree search with the addition of an array to keep track of which n-mers have been used in previously generated tags. Each time the addition of a base to the growing tag creates an n-mer already used in a previous tag, the method backtracks and tries the next value of the base.

(C) In this step, pairs of tags are compared to each other using a more sophisticated hybridization energy rule. For each pair of tags, the energy of hybridization of each tag to the complement of the other is calculated. If the energy exceeds a certain threshold, one of the tags is removed from the list. Probes are removed until there are no pairs within the list exceeding the threshold. For instance, in one embodiment, the energy rule is as follows: one point for a match (two adjacent matching base pairs), −2 points for errors in which a single base is bulged out on one strand, and −3 for all other errors including long and asymmetric loops. The highest scoring alignment between each pair of tags was determined using a dynamic programming algorithm with a preprocessor requiring a short match of at least 5 bases to initiate comparison.

More sophisticated energy rules can be incorporated in this framework by refining the hybridization rules. In addition, more complex rules for calculating the hybridization energy can be used in any of the above procedures. See, Vesnaver et al. (1989) *Proc. Natl. Acad. Sci. USA* 86, 3614–3618; Wetmur (1991) *Critical Reviews in Biochemistry and Molecular Biology* 26(3/4), 227–259, and Breslauer et al. (1986) *Proc. Natl. Acad. Sci. USA* 83, 3746–3750.

The set of tags chosen using pairwise comparison is not unique. It depends on the order of evaluation of the tags. For instance, if the tags are evaluated in alphabetical order, the final list contains more tags beginning with A than with T. A more sophisticated approach to generating the largest maximal set of such tags can also be used involving Debruijn sequences (sequences in which every n-mer for some length n occurs exactly once). For example, a Debruijn sequence incorporating all n-mers could be divided into 20 mers with overlaps of n−1, giving the maximal number of 20 mers which do not have an nmer in common. This procedure is modified to take into account the other goals for tags outlined above. For example, runs of bases are typically removed from the original Debruijn sequence, and 20 mers with imbalanced base composition or palindromes (which occur on a length scale greater than n) are deleted in a post-processing step.

Many alternative procedures for Tag selection and exclusion are possible. For example, all pairwise energies can be computed before discarding any potential tags, and the tag which has the most near-matches exceeding the energy threshold can be discarded. The remaining tag with the most near-matches (not including those to tags which have already been discarded) can be discarded. This process is repeated until there are no near-matches remaining.

For example, in one preferred embodiment of the above selection methods, the tags lack a constant region. Tags are selected by selecting all possible n-mers (e.g., 20-mers), and eliminating sequences which:

(i) have runs of 4x where x is an A, T, C, or G (e.g., AAAA);

(ii) have secondary structure in which a run of 4 contiguous nucleotides have a complementary matching run of 4 nucleotides within the tag; or (iii) have a 9 base subsequence (or other selected number of subsequences, typically from 5 to 15) in common with any other tag. All tags are then selected to have the same GC content, thereby providing all tags with similar melting temperatures when bound to a complementary probe. Performing the above steps limits the number of tags in the tag set to a pool of about 50,000 potential tags where the tags are 20-mers.

A pair-wise selection strategy is then performed to yield a final set of tags. In the pair-wise comparison, a first tag is compared to every other tag in the tag set for hybridization to the complement of the first tag. If the first tag binds to a target with a hybridization threshold a selected value higher than every other tag in the potential set it is kept. If another tag in the potential tag set binds to the complement of the first tag with a hybridization energy above the selected threshold, the first tag is discarded. This process is repeated for every tag remaining in the pool of potential tags. An exemplar computer program written in "C" is provided in Example 4 (Tags895.ccp) which performs the above selection steps. Varying the threshold resulted in sets of 0 to 50,000 tags. In one preferred embodiment, 9,000 tags were generated.

More generally, tags (or probes complementary to the tags) are selected by eliminating tags which cross-hybridize (bind to the same nucleic acid with a similar energy of hybridization). Tags bind complementary nucleic acids with a similar energy of hybridization when a complementary nucleic acid to one tag binds to another tag with an energy exceeding a specified threshold value, e.g., where one tag is a perfect match to the probe, a second tag is excluded if it binds the same probe with an energy of hybridization which is similar to the energy of hybridization of the perfect match probe. Typically if the second tag binds to the probe with about 80–95% or greater the energy of a perfectly complementary tag, or more typically about 90–95% or greater, or most typically about 95% or greater, the tag is discarded from the tag set. The calculated energy can be based upon the stacking energy of various base pairs, the energy cost for a loop in the hybridized probe-tag nucleic acid chain, and/or upon assigned values for hybridization of base pairs, or on other specified hybridization parameters. In Example 2 below, tags were selected by eliminating similar tags from a long list of possible tags, based upon hybridization properties such as assigned stacking values for tag:probe hybrids.

Methods which do not involve pairwise comparison are also used. In one embodiment, the tags were selected to comprise a constant portion and a variable portion. The variable portion of the tag sequence was limited to sequences which comprise no more than 1 C residue. The constant region of the tag sequence was chosen to be 3' (ACTC)$_4$CC (SEQ ID NO:16). This selection of specific sequences satisfies goal 7 above (the constant region was selected such that it is not self-complementary). One of skill will recognize that other constant regions can be selected, for instance where a primer binding site or restriction endonuclease site is incorporated into the tags.

Goal 2 is also met, because the probe (which is complementary to the variable portion of the tag) has no contiguous region of hybridizing bases with the exception of a single AGT or TGA sequence present on some of the probes, and even these sequences are not adjacent to the variable region of the tag where the primary hybridization occurs. In order to meet goals (1) and (8), the tags are selected to have the same length and the same total G+C content.

To prevent cross-hybridization between a tag and probes complementary to other tags, a set of tags which could not be aligned with less than two errors was chosen, wherein an "error" is either a mismatch hybridization or an overhanging nucleotide. This was done by fixing the sequence of the bases at the ends of the tags. In particular, the bases at the ends of the tags were constrained to be the same. The residues at the ends were constrained to be the same. In particular, the bases were selected to start at the 5' end with the residues GA, and to end at the 3' end with either an A or T residue, followed by a G residue. This arrangement prevents tags from matching probes with a single overhanging nucleotide and no other errors, because an overhang forces either a G-A or a G-T mismatch. This arrangement also prevents tags from matching with a single deletion error, because a single deletion would cause the probe and the tag to be misaligned at one end, causing a mismatch. One of skill will appreciate that this strategy can be modified in many ways to yield equivalent results, e.g., by selecting bases to yield C-T or C-A mismatches.

To prevent single mismatch errors in the tag-probe hybridization the next to last base from the 5' end was selected so that the number of As plus the number of Gs in the variable region is even (as noted above, the next to last base from the 5' end is either a T or an A). This base acts in a manner analogous to a parity bit in coding theory by requiring at least two differences exist between any two tags in the tag set. This is true because the GC content of all of the selected tags is the same (see, above); therefore, any base differences in the variable region have to involve the substitution of G and C residues, or T and A residues. However, the substitution of less than two bases leads to an odd number of G+A residues. Thus, at least two bases differ between any two tags in the tag set, satisfying (3) above. Similarly, the strategy could be varied, e.g., by selecting a different residue in the tag as the parity base which assigns whether the A+G content of the tag is even, or by adjusting the strategy above to yield an even number of T+G residues.

A computer program in the standard programming language "C" was written to perform each of the selection steps. For completeness, the program is provided as Example 3 below, but it is expected that one of skill can design similar programs, or perform the selection steps outlined above manually to achieve essentially similar results. Tags.ccp uses a pruned tree search to find all sequences meeting the goals above, rather than testing every sequence of a selected length for the desired sequence characteristics. While this provides an elegant selection program with few processing steps, one of skill will recognize that other programs can be used which test every potential tag for a desired sequence. Tags.ccp selects tag sets depending upon a variety of parameters including the constant sequence, the variable sequence, the GC content, the goal that the A+G ratio be even, and the relationship of the constant and variable regions in the tags of the tag set. For instance, in one experiment, a constant and a variable region were selected. The variable sequence length was selected to be 15 nucleotides in length, the G+C content of the variable region selected to be 7 nucleotides, and the A+G total number of bases was selected to be even, with a pattern of ??N$_{11}$[AT]? (SEQ ID NO:17), where ? is a selected fixed base. The parameters resulted in a set of about 8,000 tag sequences.

More generally, the problem of designing a set of tag sequences which do not cross-hybridize has strong similarities to the problem of designing error-correcting codes in coding theory. The primary difference is that insertions and deletions do not have a correlate in coding theory. This problem, is accounted for as shown above by having constant regions within the probe sequences. The strategy is generalized by changing the location of the parity bit, the required parity, or the locations of the constant regions. More complex codes are also useful, for example codes which require more differences between pairs of tags. See, Blahut (1983) *Theory and Practice of Error Control Codes* Addison-Wesley Publishing Company, Menlo Park, Calif.

One of skill will also recognize that pairwise comparison methods are used in conjunction with any other selection method. For instance, the tags generated according to specified rules such as those implemented by tags.ccp can be further selected using any of the pairwise comparison methods described herein.

Synthesis of Oligonucleotide Arrays

Oligonucleotide arrays are selected to have oligonucleotides complementary to the tag nucleic acids described above. The synthesis of oligonucleotide arrays generally is known. The development of very large scale immobilized polymer synthesis (VLSIPS™ ) technology provides methods for arranging large numbers of oligonucleotide probes in very small arrays. Pirrung et al., U.S. Pat. No. 5,143,854 (see also PCT Application No. WO 90/15070), McGall et al., U.S. Pat. No. 5,412,087, Chee et al. SN PCT/U.S.94/12305, and Fodor et al., PCT Publication No. WO 92/10092 describe methods of forming vast arrays of oligonucleotides using, for example, light-directed synthesis techniques. See also, Fodor et al. (1991) *Science* 251:767–777; Lipshutz et al. (1995) *BioTechniques* 19(3): 442–447; Fodor et al. (1993) *Nature* 364: 555–556; and Medlin (1995) *Environmental Health Perspectives* 244–246.

As described above, diverse methods of making oligonucleotide arrays are known; accordingly no attempt is made to describe or catalogue all known methods. For exemplary purposes, light directed VLSIPS™ methods are briefly described below. One of skill will understand that alternate methods of creating oligonucleotide arrays, such as spotting and/or flowing reagents over defined regions of a solid substrate, bead based methods and pin-based methods are also known and applicable to the present invention (See, e.g., U.S. Pat. No. 5,384,261, incorporated herein by reference for all purposes). In the methods disclosed in these applications, reagents are typically delivered to the substrate by flowing or spotting polymer synthesis reagents on predefined regions of the solid substrate.

Light directed VLSIPS™ methods are found, e.g., in U.S. Pat. Nos. 5,143,854 and 5,412,087. The light directed methods discussed in the '854 patent typically proceed by activating predefined regions of a substrate or solid support and then contacting the substrate with a preselected monomer solution. The predefined regions are activated with a light source, typically shown through a photolithographic mask. Other regions of the substrate remain inactive because they are blocked by the mask from illumination. Thus, a light pattern defines which regions of the substrate react with a given monomer. By repeatedly activating different sets of predefined regions and contacting different monomer solutions with the substrate, a diverse array of oligonucleotides is produced on the substrate. Other steps, such as washing unreacted monomer solution from the substrate, are used as necessary.

The surface of a solid support is typically modified with linking groups having photolabile protecting groups (e.g., NVOC or MeNPoc) and illuminated through a photolithographic mask, yielding reactive groups (e.g., typically hydroxyl groups) in the illuminated regions. For instance, during oligonucleotide synthesis, a 3'-O-phosphoramidite (or other nucleic acid synthesis reagent) activated deoxynucleoside (protected at the 5'-hydroxyl with a photolabile group) is presented to the surface and coupling occurs at sites that were exposed to light in the previous step. Following capping, and oxidation, the substrate is rinsed and the surface illuminated through a second mask, to expose additional hydroxyl groups for coupling. A second 5'-protected, 3'-O-phosphoramidite activated deoxynucleoside (or other oligonucleotide monomer as appropriate) is then presented to the resulting array. The selective photodeprotection and coupling cycles are repeated until the desired set of oligonucleotides is produced.

In addition to VLSIPS™ arrays, other probe arrays can also be made. For instance, standard Southern or northern blotting technology can be used to fix nucleic acid probes to various substrates such as papers, nitrocellulose, nylon and the like. Because the formation of large arrays using standard technologies is difficult, VLSIPS™ arrays are preferred.

Making Tag Nucleic Acids and Oligonucleotides to be Coupled into Arrays: Synthesis of Test Nucleic Acids: Cloning of Tag Nucleic Acids into Cells As described above, several methods for the synthesis of oligonucleotide arrays are known. In preferred embodiments, the oligonucleotides are synthesized directly on a solid surface as described above. However, in certain embodiments, it is useful to synthesize the oligonucleotides and then couple the oligonucleotides to the solid substrate to form the desired array. Similarly, nucleic acids in general (e.g., tag nucleic acids) can be synthesized on a solid substrate and then cleaved from the substrate, or they can be synthesized in solution (using chemical or enzymatic procedures), or they can be naturally occurring (i.e., present in a biological sample).

Molecular cloning and expression techniques for making biological and synthetic oligonucleotides and nucleic acids are known in the art. A wide variety of cloning and expression and in vitro amplification methods suitable for the construction of nucleic acids are well-known to persons of skill. Examples of techniques and instructions sufficient to direct persons of skill through many cloning exercises for the expression and purification of biological nucleic acids (DNA and RNA) are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook); and *Current Protocols in Molecular Biology*, F. M. Ausubel et al, eds., Current Protocols, a joint venture between Greene Publishing Associates, Inc. and John Wiley & Sons, Inc., (1994 Supplement) (Ausubel). Nucleic acids such as Tag nucleic acids can be cloned into cells (thereby creating recombinant tagged cells) using standard cloning protocols such as those described in Berger, Sambrook and Ausbel.

Examples of techniques sufficient to direct persons of skill through in vitro methods of nucleic acid synthesis and amplification of tags and probes in solution, including enzymatic methods such as the polymerase chain reaction (PCR), the ligase chain reaction (LCR), Qβ-replicase amplification (QBR), nucleic acid sequence based amplification (NASBA), strand displacement amplification (SDA), the cycling probe amplification reaction (CPR), branched DNA (bDNA) and other DNA and RNA polymerase mediated techniques are known. Examples of these and related techniques are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Amheim & Levinson (Oct. 1, 1990); WO 94/11383; Vooijs et al. (1993) *Am J. Hum. Genet.* 52: 586–597; *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Sooknanan and Malek (1995) *Bio/Technology* 13, 563–564; Walker et al. *Proc. Natl. Acad. Sci. USA* 89, 392–396), and Barringer et al. (1990) *Gene* 89, 117. Improved methods of cloning in vitro amplified nucleic acids are described in Wallace et al., U.S. Pat. No. 5,426,039. In one preferred embodiment, nucleic acid tags are amplified prior to hybridization with VLSIPS™ arrays as described above. For instance, where tag nucleic acids are cloned into cells in a cellular library, the tags can be amplified using PCR.

Standard solid phase synthesis of nucleic acids is also known. Oligonucleotide synthesis is optionally performed on commercially available solid phase oligonucleotide synthesis machines (see, Needham-VanDevanter et al. (1984) *Nucleic Acids Res.* 12:6159–6168) or manually synthesized using the solid phase phosphoramidite triester method described by Beaucage et. aL (Beaucage et. al. (1981) *Tetrahedron Letts.* 22 (20): 1859–1862). Finally, as described above, nucleic acids are optionally synthesized using VLSIPS™ methods in arrays, and optionally cleaved from the array. The nucleic acids can then be optionally reattached to a solid substrate to form a second array where appropriate, or used as tag nucleic acids where appropriate, or used as tag sequences for cloning into a cell.

Labels

The term "label" refers to a composition detectable by spectroscopic, photochemical, biochemical, immunochemical, or chemical means. For example, useful nucleic acid labels include 32P, 35S, fluorescent dyes, electron-dense reagents, enzymes (e.g., as commonly used in an ELISA), biotin, dioxigenin, or haptens and proteins for which antisera or monoclonal antibodies are available.

A wide variety of labels suitable for labeling nucleic acids and conjugation techniques are known and are reported extensively in both the scientific and patent literature, and are generally applicable to the present invention for the labeling of tag nucleic acids, or amplified tag nucleic acids for detection by the arrays of the invention. Suitable labels include radionucleotides, enzymes, substrates, cofactors, inhibitors, fluorescent moieties, chemiluminescent moieties, magnetic particles, and the like. Labeling agents optionally include e.g., monoclonal antibodies, polyclonal antibodies, proteins, or other polymers such as affinity matrices, carbohydrates or lipids. Detection of tag nucleic acids proceeds by any known method, including immunoblotting, tracking of radioactive or bioluminescent markers, Southern blotting, northern blotting, southwestern blotting, northwestern blotting, or other methods which track a molecule based upon size, charge or affinity. The particular label or detectable group used and the particular assay are not critical aspects of the invention. The detectable moiety can be any material having a detectable physical or chemical property. Such detectable labels have been well-developed in the field of gels, columns, solid substrates and in general, labels useful in such methods can be applied to the present invention. Thus, a label is any composition detectable by spectroscopic, photochemical, biochemical, immunochemical, electrical, optical or chemical means. Useful labels in the present invention include fluorescent dyes (e.g., fluorescein isothiocyanate, Texas red, rhodamine, and the like), radiolabels (e.g., 3H, 125I, 35S, 14C, or 32P), enzymes (e.g., LacZ, CAT, horse radish peroxidase, alkaline phosphatase and others, commonly used as detectable enzymes, either as marker gene products or in an ELISA), nucleic acid intercalators (e.g., ethidium bromide) and colorimetric labels such as colloidal gold or colored glass or plastic (e.g. polystyrene, polypropylene, latex, etc.) beads.

The label is coupled directly or indirectly to the desired nucleic acid according to methods well known in the art. As indicated above, a wide variety of labels are used, with the choice of label depending on the sensitivity required, ease of conjugation of the compound, stability requirements, available instrumentation, and disposal provisions. Non radioactive labels are often attached by indirect means. Generally, a ligand molecule (e.g., biotin) is covalently bound to a polymer. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody. Labels can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. For detection in VLSIPS™ arrays, fluorescent labels and detection techniques, particularly microscopy are preferred. Similarly, enzymatic labels may be detected by providing appropriate substrates for the enzyme and detecting the resulting reaction product. Finally, simple colorimetric labels are often detected simply by observing the color associated with the label. Thus, in various dipstick assays, conjugated gold often appears pink, while various conjugated beads appear the color of the bead.

Substrates

As mentioned above, depending upon the assay, the tag nucleic acids, or probes complementary to tag nucleic acids can be bound to a solid surface. Many methods for immobilizing nucleic acids to a variety of solid surfaces are known in the art. For instance, the solid surface is optionally paper, or a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass, silica, plastic, metallic or polymer bead or other substrate as described herein. The desired component may be covalently bound, or noncovalently attached to the substrate through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which are appropriate depending on the assay include paper, glasses, ceramics, metals, metalloids, semiconductive materials, cements and the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials are optionally employed, e.g., as laminates, to obtain various properties. For example, protein coatings, such as gelatin can be used to avoid non specific binding, simplify covalent conjugation, enhance signal detection or the like. If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. In addition to covalent bonding, various methods for noncovalently binding an assay component can be used.

EXAMPLES

The following examples are provided by way of illustration only and not by way of limitation. Those of skill will readily recognize a variety of noncritical parameters which could be changed or modified to yield essentially similar results.

Example 1
Parallel Analysis of Deletion Stains of *S. cerevisie*.

The complete sequence of the *S. cerevisiae* genome is known. In the process of sequencing the genome, thousands of open reading frames, representing potential genes or gene fragments were identified. The function of many of these ORFs is unknown.

Gene disruption is a powerful tool for determining the function of unknown ORFs in yeast. Given the sequence of an ORF, it is possible to generate a deletion strain using standard gene disruption techniques. The deletion strain is then grown under a variety of selective conditions to identify a phenotype which reveals the function of the missing ORF. However, individual analysis of thousands of deletion strains to assess a large number of selective conditions is impractical.

To overcome this problem, individual ORF deletions were tagged with a distinguishing molecular tag. The deletion specific tags were read by hybridization to a high density array of oligonucleotide probes comprising probe sets complementary to each tag.

The molecular tagging strategy involves a four-step approach for generating tagged deletion strains that can be pooled and analyzed in parallel through selective growth assays.

Figure 2:
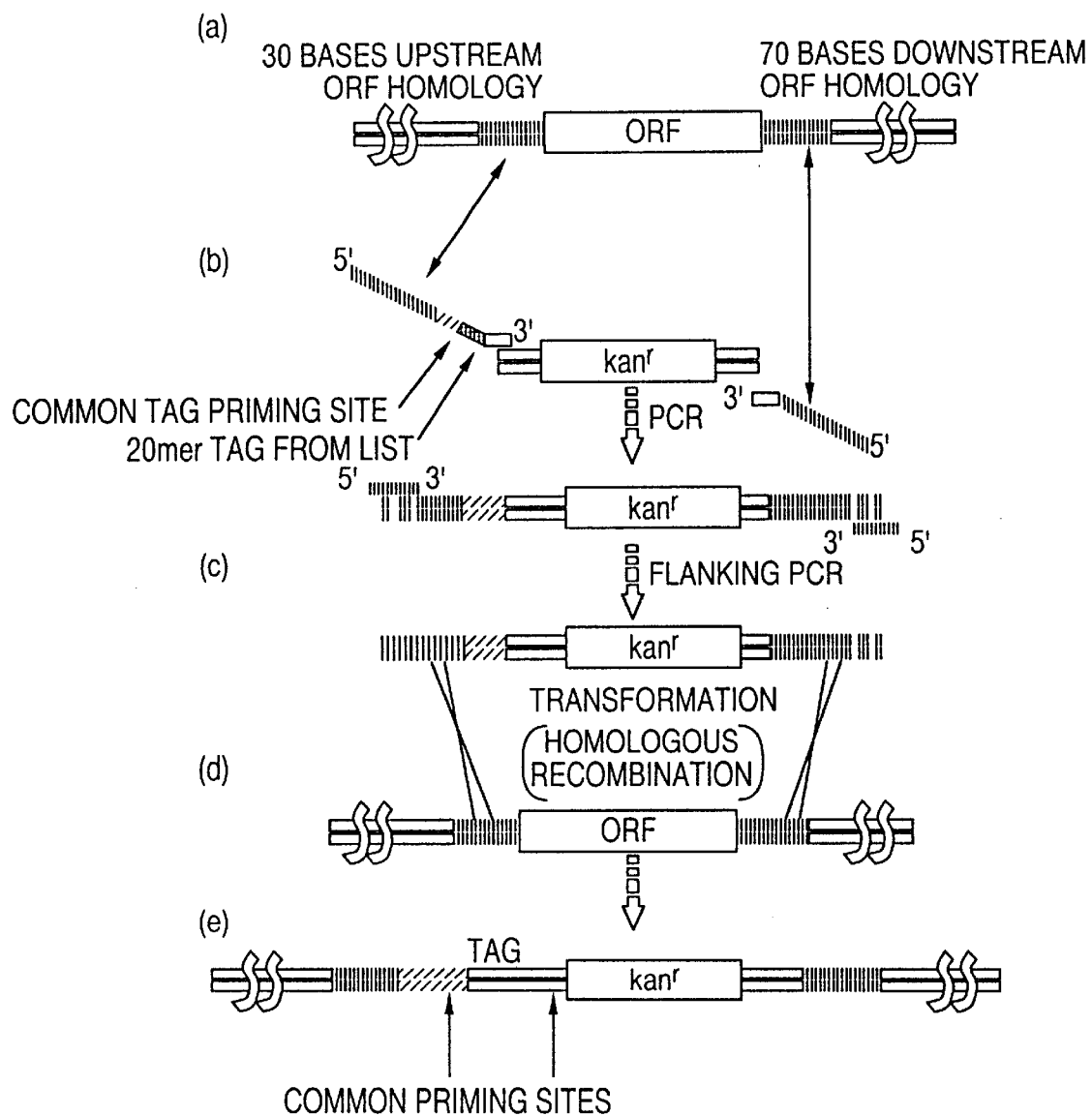
FIG. 2 shows a PCR-targeting strategy used to generate tagged deletion strains. (a) The ORF is identified from the sequence information in the database. Regions immediately flanking the ORF are used to generate the deletion strain. (b) The selectable marker (kan$^r$) is amplified using a pair of long primers to generate an ORF specific deletion construct. The upstream 86 mer primer consists of (5' to 3'): 30 bases of yeast homology, an 18 base common tag priming site, a 20 base molecular tag, and a 22 base sequence that is homologous to one side of the marker. The down-stream oligonucleotides consists of 50 bases of yeast homology to the other side of the targeted ORF and 16 bases that are homologous to the other side of the marker. The dashed lines representing the long oligonucleotides illustrates that the primers are unpurified and are missing sequence on the 5' end. (c) A second round of PCR with 20 mers homologous to the ends of the initial PCR product was used to "flush" the ragged ends generated by unpurified oligonucleotide in the first round. (d) The resulting marker flanked by yeast ORF homology on either side is transformed directly into haploid yeast strain and homologous recombination results in the replacement of the targeted ORF with the marker, 20 mer tag, and tag priming site.
Figure 5:
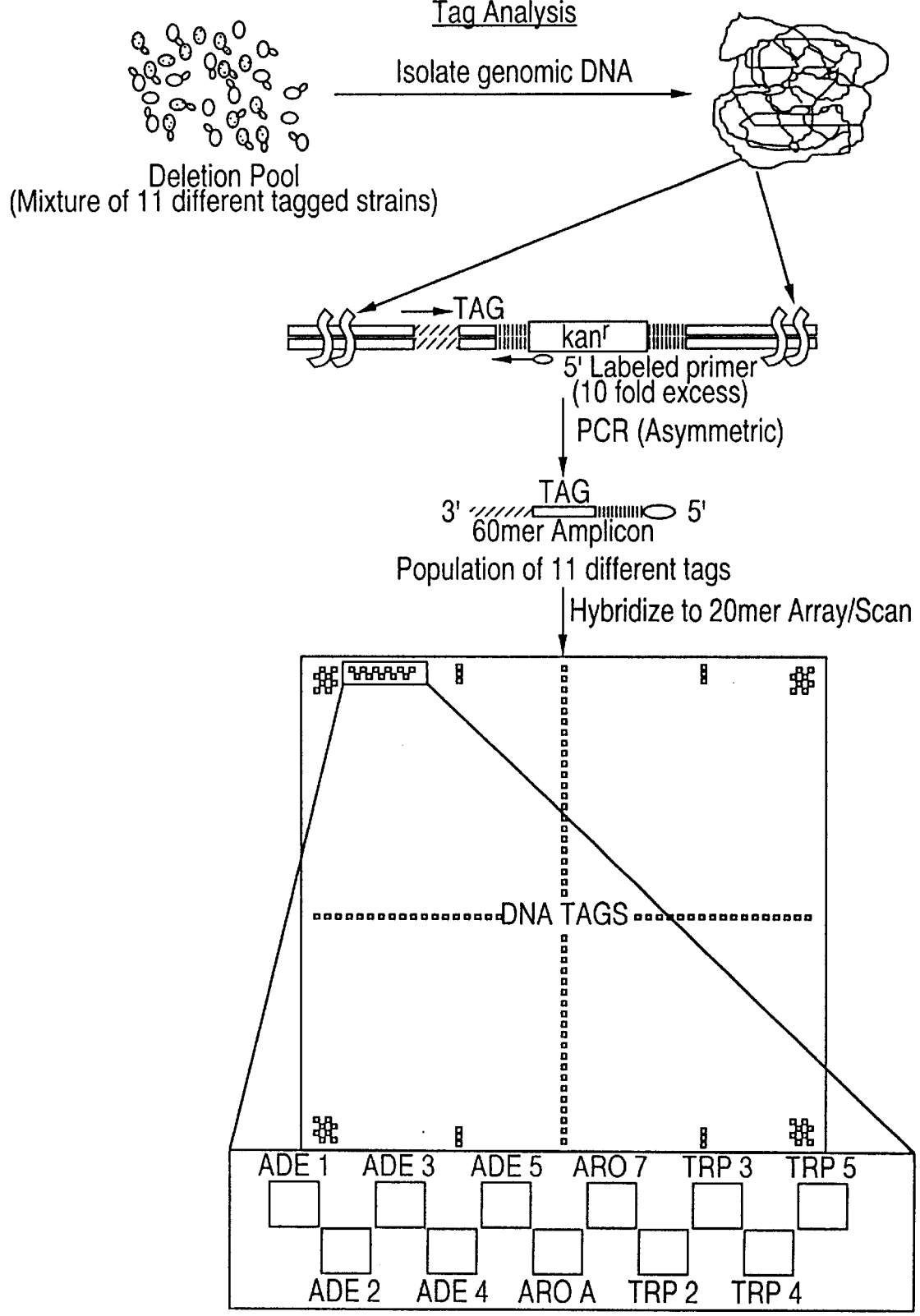
FIG. 5 shows the Tag amplification strategy described in Example 1. (a) A deletion pool was generated by combining equal numbers of the eleven tagged deletion strains described in FIG. 3. Genomic DNA isolated from a representative aliquot of the pool was used as template for a tag amplification reaction. (b) Tags were amplified using a single pair of primers that are homologous to the common priming sites which flank each tag. One of the common primers is labeled with 5' flourescein and included in a 10-fold excess over the unlabeled primer. (c) The asymmetric nature of the PCR generates a population of single-stranded flourescently labeled 60 mer tag amplicons that are directly hybridized the high-density 20 mer array which is then washed and scanned. (d) A depiction of an actual scanned image of the array shows the (predicted) hybridization pattern for the tags with virtually no cross-hybridization on the rest of the chip. White boxes (□) within the array represent positive binding of an oligonucleotide to the sequence at that position in the array. A closeup view of the left hand comer shows the location of the tags for each of the different deletion strains.

Individual deletion strains were generated using a PCR-targeting strategy (Baudin, Ozier-Kalogeropoulos et aL 1993 *Nuc. Acids Res.* 21(14): 3329–3330). ORF specific molecular tags were incorporated during the transformation (FIG. 2). Tagged deletion strains were pooled and representative aliquots grown under different selective conditions. The molecular tags were amplified from the surviving strains and hybridized to a high-density array containing complements to the tag sequences (FIG. 2). The array was then washed and scanned using a highly sensitive confocal microscope. The normalized signal for each tag reflects the relative abundance of the different deletion strains in the pool. The fitness of the deletion strains in the pool was determined by comparing the hybridization patterns obtained before and after the selective growth.

To test the feasibility of the molecular tagging strategy, a list of 9,105 unique 20 mer tag sequences was generated using the computer program tags.ccp (See, below and Table 1).

TABLE 1

|  | Selection criteria | Properties of selected 20 mers | Number of 20 mers accepted |
| --- | --- | --- | --- |
| All Possible 20 mers | None |  | $1.2 \times 10^{12}$ |
| Primary Filter | No hairpins > 4 bp | Similar Tm(+/−7° C.) |  |
|  | No single nucleotide runs > 4 bases | Good hybridization | 51,081 |
|  | Similar base composition (4–6 of each base) | No extreme homology |  |
|  | No common 9 mers |  |  |
| Secondary Filter | Low stringency pair-wise analysis | Unique | 51,081 |

TABLE 1-continued

| Selection criteria | Properties of selected 20 mers | Number of 20 mers accepted |
|---|---|---|
| . | . | 9,105 -> (4,500 selected at random) |
| . | . | 2,643 |
| . | . | 853 |
| . | . | 170 |
| Highest stringency comparisons | Very unique | 42 |

A 1.28 cm×1.28 cm array comprising probes complementary to the tag sequences was produced by standard light-directed VLSIPS™ methods. The resulting high-density array of probes provides probe sets at known locations in the array. Fluorescence imaging using a scanning confocal microscope permitted quantitation of the hybridization signals for each of the 4,500 sets of 20 mers on the array (FIG. 1). Hybridization experiments with 120 different fluorescently labeled 20 mer oligonucleotides showed that the arrays are sensitive, quantitative, and highly specific.

As part of a feasibility study, tagged deletion strains were generated for eleven characterized auxotrophic yeast genes (ADE1, ADE2, ADE3, ADE4, ADE5, AROA, AR07, TRP2, TRP3, TRP4, and TPR5) using the strategy described in FIG. 2. The oligonucleotides used to generate the deletion strains are described in FIG. 3 and transformation results are shown in FIG. 4.

Figure 6A:
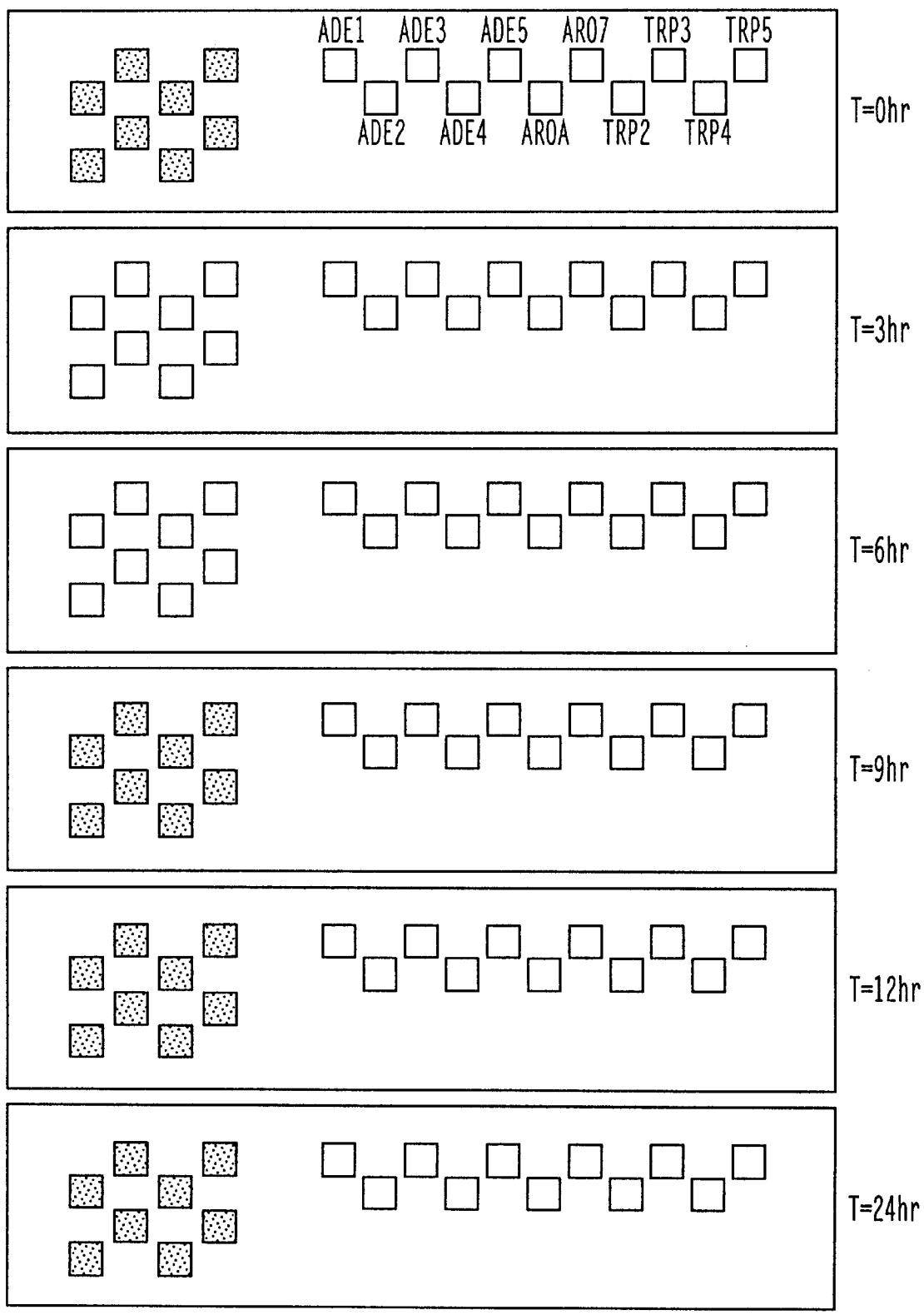
FIG. 6 depicts the analysis of a deletion pool containing 11 tagged auxotrophic deletion strains. A deletion pool was generated by combining equal numbers of cells from each of the 11 deletion strains described in FIG. 3. Representative aliquots were grown in (A) complete media (COMPLETED MEDIA; SDC), (B) media missing adenine (ADE DROP-OUT MEDIA; SDC-ADE), (C) or media missing tryptophan (TRP DROP-OUT MEDIA; SDC-TRP). Cells were harvested at the indicated time points and genomic DNA was isolated. Tags were amplified from the genomic DNA and labeled amplicons were directly hybridized to the high-density array for 30 minutes, washed, and scanned. A blowup of the upper left hand comer for each of the scans is shown. White boxes (□) within the array represent positive binding of an oligonucleotide to the sequence at that position in the array. Black boxes (■) within the array represent a lack of binding of an oligonucleotide to the sequence at that position in the array. Grayed boxes represent partial binding.
Figure 6C:
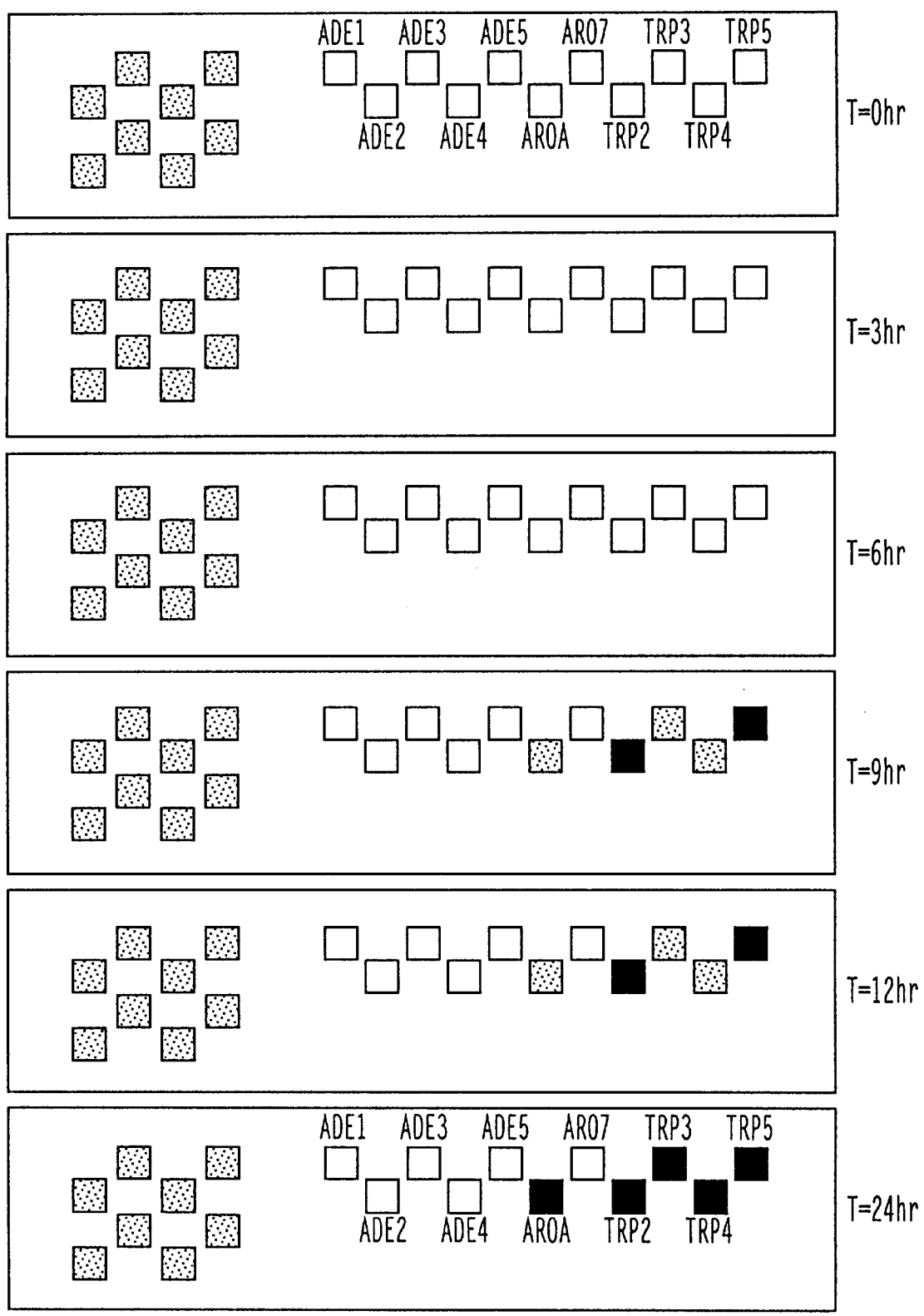

The strains were pooled and grown in complete media and different drop-out medias. Genomic DNA extracted from the pool served as a template for an asymmetric tag amplification using a pair of primers homologous to common regions flanking each tag (FIG. 4). Depletion of specific strains from the pool was quantitatively measured by hybridizing the amplified tags to the high-density arrays (FIGS. 6A–C).

Example 2
A Method for Selecting Tags From a Pool of Tags

Tags (or probes complementary to the tags) are selected by eliminating tags which bind to the same target with a similar energy of hybridization. Tags bind complementary nucleic acids with a similar energy of hybridization when a complementary nucleic acid to one tag binds to another tag with an energy exceeding a specified threshold value. The calculated energy is based upon, e.g., the stacking energy of various base pairs, and the energy cost for a loop in the chain, and/or upon assigned values for hybridization of base pairs, or on other specified hybridization parameters. In this example, tags were selected by eliminating similar tags from a long list of possible tags, based upon hybridization properties such as assigned stacking values for tag:probe hybrids.

Probecmp was written to create a list of non-similar tags from a long list of tags. Tags are considered to be similar if a perfect match to one tag binds to another tag with an energy exceeding some specified threshold. Probecmp incorporates three distinct ideas in selecting tags. The ideas are:

1) a stacking and loop cost model for the calculation of hybridization energy;
2) algorithms to quickly calculate that energy, including a recursive, heavily pruned algorithm, and a dynamic programming algorithm; and
3) a hash table to quickly find perfect match segments.

The Stacking and Loop Cost Model for the Calculation of Hybridization Energy

The calculated energy is based on the stacking energy of various base pairs, and the energy cost for a loop in the chain. E.g., the user can specify that the energy from an TA stacking is 2, and the GC and CG is 4, and AC, AG, TC, GT, or TG is 3. With these values, A G G T A C G is worth 3+4+3+2+3+4=19. The energy cost for loops is given by a matrix of the loop size on each strand:

|   | 0 | 1 | 2 | 3 |
|---|---|---|---|---|
| 0 | 0 | 5 | 10 | 10 |
| 1 | 5 | 0 | 5 | 10 |
| 2 | 10 | 5 | 5 | 10 |
| 3 | 10 | 10 | 10 | 10 |

For example, if the following match occurs, there is a loop size of 1 on the first strand and 0 on the second strand. Examination of the table reveals a loop penalty of 5, and a resulting stacking energy of 14.

```
                    C
    target:  A G G T A C G
    tag:     T C C A T G C
```

The Algorithms to Quickly Calculate the Energy of Hybridization

The hybridization energy can be calculated using either a recursive algorithm, or a dynamic programming algorithm. The recursive algorithm is fast if the energy cost for loops is large relative to the stacking energy. The dynamic programming algorithm is fast if the energy cost for loops is small relative to the stacking energy.

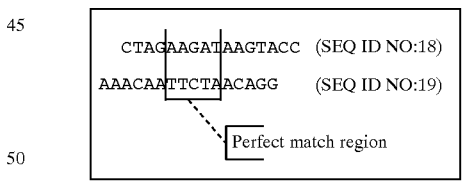

Both energy calculation algorithms start out with 2 tags which have a multiple base perfect match sequence. They then calculate the energy of the perfect match sequence, then find the matches that lead to the highest energy before the perfect match region, and after the perfect match region. The total matching energy is the sum of these three energies. Since this model does not have an implied direction, the same algorithm can be used for both the before match energy, and the after match energy, by reversing the orders of the before match fragments.

A Recursive, Heavily Pruned Algorithm

The recursive algorithm tries all match trees, looking at all loop sizes that have a low enough cost that they can be paid for with the maximum possible energy for the remaining matches. Code for the algorithm is as follows:

```
/* linkSet is a structure listing locations of matching bases, and the corresponding energy. */
static linkSet local * calculateEnergyAndLinksFromPointOn(short pp, short tp, char local * tag,
                char local *target, short basesLeftInTag, short basesLeftInTarget) {
        register short i, j;
        float tempEnergy, bestEnergy = 0;
        linkSet *en, *returnValue = NULL;
        short maxTagLoop;
        maxTagLoop = min(basesLeftInTag, maxLegalLoop + 1); // only check legal loop sizes
        for(i = 0; i <maxTagLoop; i ++) { // i is loop size along tag
                // bother with loop is an array that has precalculated the minimum number of base
                  pairs
needed to pay for that loop size.
                for(j = 0; min(basesLeftInTag - i, basesLeftInTarget - j) > botherWithLoop[i][j];
j ++) { // j is loop size along target
                        if( (tag[pp + i + 1] & target[tp + j + 1])){ // this tests that the tag matches
the target
                                en = calculateEnergyAndLinksFromPointOn(pp + i + 1, tp + j + 1, tag,
target, basesLeftInTag - i–1, basesLeftInTarget - j-1);
                                // if this is the last match, and the stacking energy pays for the loop, and
is better than our previous best . . .
                                if(en == NULL && (tempEnergy =
(stackingEnergy[target[tp]] [target[tp + j 1]]- loopEnergy[i][j])) > bestEnergy ){
                                        returnValue = makeNewLinkset(returnValue);
                                        returnValue->energy = bestEnergy = tempEnergy;
                                        if(i == 0 && j == 0) { // add self and successor as link
                                        firstLink(returnValue, 2, pp, tp );
                                        }else{ // add successor as link
                                                firstLink(returnValue, 1, pp + i + 1, tp + j + 1);
                                        addNewLink(returnValue, 1, pp, tp);
                                        }
                                } else if((i == 0) && (j == 0)){// new matching base pair is adjacent to
old one
                                // if the stacking energy pays for the loop, and is better than our
previous best . . .
                                        if((tempEnergy = en->energy +
stackingEnergy[target[tp]][target[tp + j + 1]] - loopEnergy[i][j]) > bestEnergy){
                                                en->energy = bestEnergy = tempEnergy;
                                                makeFirstLinkOneLonger(en);
                                                if(returnValue ! = NULL) farfree(returnValue);
                                                returnValue = en;
                                                }else // new energy to small, don't want it, just free it.
                                                        if(en ! = NULL)farfree(en);
                                }else { // loop size is non-zero
                                        // if the stacking energy pays for the loop, and is better than our
previous best . . .
                                        if((tempEnergy = en-> energy +
stackingEnergy[target[tp] [target[tp + j + 1]] - loopEnergy[i][j]) > bestEnergy){
                                                en->energy = bestEnergy + tempEnergy
                                                if(returnValue ! = NULL) farfree(returnValue);
                                                returnValue = en;
                                        addNewLink(returnValue, 1, pp, tp);
                                        } else // new energy to small, don't want it, just free it.
                                                if(en ! = NULL) farfree(en);
                                }
                        }
                }
        }
        return returnValue;
}
```

A Dynamic Programming Algorithm

The dynamic programming algorithm starts out by making a matrix of permitted or "legal" connections between the two fragments.

```
CTAGAAGATAAGTACC   (SEQ ID NO:18)

AAACAATTCTAACAGG   (SEQ ID NO:19)

Perfect match region
```

Then, starting at the upper left corner, each legal connection is considered, and all previous bases are identified. Previous bases are any legal base pair in the rectangle to the upper left of the considered base. In the figure below, the first three legal matches have no previous legal connection except the (assumed) perfect match which occurs before the mismatch segment.

|   | A | A | G | T | A | C | C |
|---|---|---|---|---|---|---|---|
| A | 0 | 0 | 0 | 1 | 0 | 0 | 0 |
| A | 0 | 0 | 0 | 1 | 0 | 0 | 0 |
| C | 0 | 0 | 0 | 1 | 0 | 0 | 0 | 0 |
| G | 0 | 0 | 0 | 0 | 0 | 0 | 1 | 1 |
| G | 0 | 0 | 0 | 0 | 0 | 0 | 1 | 1 |

The values in those cells are replaced by the sum of the stacking energy, and the loop cost.

|   | A | A | G | T | A | C | C |
|---|---|---|---|---|---|---|---|
| A | 0 | 0 | 0 | -3 | 0 | 0 | 0 |
| A | 0 | 0 | 0 | 5 | 0 | 0 | 0 |
| C | 0 | 0 | 8 | 0 | 0 | 0 | 0 |
| G | 0 | 0 | 0 | 0 | 0 | 1 | 1 |
| G | 0 | 0 | 0 | 0 | 0 | 1 | 1 |

Then the process is repeated for each legal connection further out in the matrix. If there is more than one legal loop, the loop with the maximum value is used. When this process is finished, path that resulted in the maximum cell value is the best match.

|   | A | A | G | T | A | C | C |
|---|---|---|---|---|---|---|---|
| A | 0 | 0 | 0 | -3 | 0 | 0 | 0 |
| A | 0 | 0 | 0 | 5 | 0 | 0 | 0 |
| C | 0 | 0 | 8 | 0 | 0 | 0 | 0 |
| G | 0 | 0 | 0 | 0 | 0 | 1 | 1 |
| G | 0 | 0 | 0 | 0 | 0 | 1 | 1 |

A Hash Table to Quickly Find Perfect Match Segments

To speed up the comparison of one tag with all other tags in the list, the program uses a hash table which points to all occurrences of any given n-mer in the set of tags. The hash table is implemented as two arrays of structures which point to locations in tags. The first array is 4 to the n records long, and the second is the size of the complete list of tags.

Example 3
"Tags.ccp"

The computer program tags.ccp, written in "C" and referred to above is provided on the Computer Program Listing Appendix compact disk.

Example 4
Tags895.ccp

A preferred method of selecting probe arrays involves discarding all probes from a pool of probes which have identical 9 mer runs (thereby eliminating many tags which will cross-hybridize), followed by pair-wise comparison of the remaining tag nucleic acids and elimination of tags which hybridize to the same target. An exemplar program (tags895.ccp) written in "C" is provided on the Computer Program Listing Appendix compact disk.

A truncated output list is provided below: /SAMPLE OUTPUT FILE FOR TAGS895.CPP / AAACAAACAC-CCGCGTGGTT AAACAAAGACCCGCCGGTGT AAA-CAAATACCCGCCGTGGG AAACAACAACCCGCGT-GTGG AAACAACCAACCCGGTGTGG AAACAACGAACCCGCTGGTG AAACAACTAAC-CCGCTGTGG AAACAAGAACCCGCCGTTGG AAA-CAAGCAACCCGGCGTGT AAACAAGGAACCCGC-CTGGT AAACAAGTAACCCGCCTTTG AAACAATAACCCGCGCTGGG AAACAATCAAC-CCGCTTGGG AAACAATGAACCCGCGTCGG AAA-CAATTAACCCGCGTTCG AAACACAAACCCGGCTG-GTG AAACACACAACCCGTGGTGG AAACACAGAACCCGCTTTGG AAACACATAACCCG-GCGGTG AAACACCAAACCCGTTGTGG AAACAC-CCAAACCGTTGTGG AAACACCGAAACCCTGTGGG

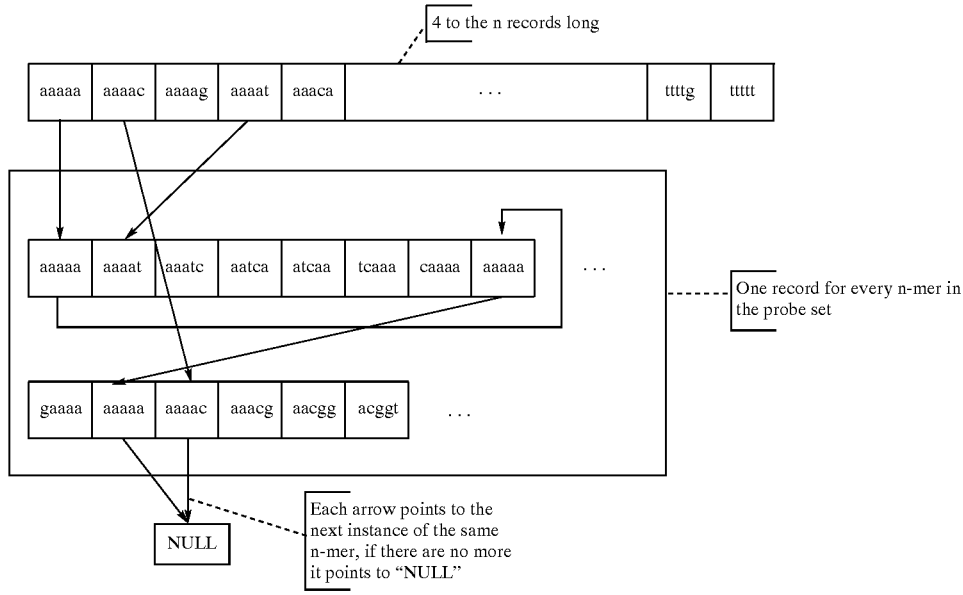

One record for every n-mer in the probe set

Each arrow points to the next instance of the same n-mer, if there are no more it points to "NULL"

Thus, a file is created with a list of all of the tags (or probes) from which desired tags are to be selected. Typically, the tags are listed one per line, in a column, e.g., with the heading "probe" or "tag." The above analysis is performed on the file, and an output file is produced based on the above method resulting in a list of tags in which no tag hybridizes to the complement of any other tag with a stacking energy which exceeds a specified threshold.

AAACACCTAAACCCTTGTGG AAACACGAAACCCG-GTCGGT AAACACGCAAACCCGGTGGT AAACACG-GAAACCCTCGGTG AAACACGTAAACCCGTCGGT AAACACTAAACCCGTGCGGT AAACACTCAAAC-CCTGGTGG AAACACTGAAACCCGTCTGG AAA-CACTTAAACCCGTTCGG AAACAGAAACCCGCTCG-GTG AAACAGACAACCCGGCTTGG AAACAGAGAACCCGGCCTTG AAACAGATAAC-CCGCTCTTG AAACAGCAAACCCGTGGCGT AAA-CAGCCAAACCGCGTGGT //many lines removed here //

Tag Count: 14507

All publications and patent applications cited in this specification are herein incorporated by reference for all purposes as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for selecting a set of tag nucleic acids, said method comprising:
   (a) providing a plurality of candidate tag nucleic acid sequences, wherein the total number of nucleotides in each tag nucleic acid sequence is identical, the number of G+C nucleotides in each tag nucleic acid sequence is identical and the overall number of A+G nucleotides in each of the tag nucleic acids sequences is even;
   (b) aligning a first candidate tag with each of the other candidate tags in the plurality;
   (c) excluding the first candidate tag from the plurality if it can be aligned with less than two errors to another candidate tag, wherein an error is either a mismatch hybridization or an overlapping nucleotide,
   (d) repeating (b) and (c) for each of the remaining candidate tags in the plurality, thereby providing a set of nucleic acid tags; and
   (e) synthesizing at least 100 members of the set of nucleic acid tags.

2. A method for selecting a set of tag nucleic acids, wherein each tag nucleic acid sequence comprises a constant region and a variable region, said method comprising:
   (a) providing a plurality of candidate tag nucleic acid sequences;
   (b) aligning a selected candidate tag with each of the other candidate tags in the plurality;
   (c) excluding the selected candidate tag if it can be aligned with less than two errors in the variable region to another candidate tag, wherein an error is either a mismatch hybridization or an overlapping nucleotide;
   (d) repeating (b) and (c) for each of the remaining candidate tags in the plurality, thereby providing a set of nucleic acid tags; and
   (e) synthesizing members of the set of nucleic acid tags.

3. A composition comprising a set of tag nucleic acids to individually detect members of a plurality of tagged components in a mixture of tagged components, which set of tag nucleic acid sequences comprises a plurality of at least 100 different tag nucleic acid sequences, which tag nucleic acid sequences comprise a variable region and a constant region;
   which variable region for each tag nucleic acid sequence in the set of tag nucleic acid sequences has the same $T_m$, the same G+C to A+T ratio, the same length, does not cross-hybridize under stringent conditions to any other tag nucleic acid sequence variable region, and does not cross-hybridize under stringent conditions to the complement of any other tag nucleic acid sequence variable region;
   wherein the variable regions of the tag nucleic acid sequence in the set of tag nucleic acid sequences cannot be aligned with less than two differences between any two of the tag nucleic acid sequences in the set of tag nucleic acid sequences, and
   further wherein each member of the set of nucleic acid tags is comprised of a single nucleic acid sequence from the set of nucleic acid tags.

4. The composition of claim 3, wherein the variable region of each of the tag nucleic acid sequences in the tag nucleic acid sequence set comprises less than two C nucleotides.

5. The composition of claim 3, wherein the variable region of the tag nucleic acid sequence from the set of tag nucleic acid sequences comprises an even number of A+G nucleotides.

6. A set of at least 100 different tag nucleic acids selected according to the mothod of 104.

7. A set of at least 100 different tag nucleic acids wherein each member of the set:
   (a) does not have a region of complementarity with any other member of the set greater than four nucleotides;
   (b) does not have a selected length of contiguous nucleotides in common with any other tag nucleic acid sequence in the set, wherein the length is selected from the following: 5, 6, 7, 8, 9, 10, 11, 12, 13, 14 or 15;
   (c) has greater than 5 differences out of 20 nucleotides when aligned for maximal sequence correspondence with any other tag nucleic acid sequence in the set, and
   (d) does not have four contiguous nucleotides selected from the group consisting of four X residues, four Y residues and four Z residues, wherein X is G or C, Y is G or A, and Z is A or T, and
   (e) each member of the set of tag nucleic acids is comprised of a single nucleic acid sequence from the set of nucleic acid tags.

8. A set of at least 100 different tag nucleic acids wherein:
   (a) no two members of the set can be aligned with less than two errors, wherein an error is either a mismatch hybridization or an overhanging nucleotide;
   (b) the total number of nucleotides in each tag nucleic acid sequence is identical;
   (c) the number of G+C nucleotides in each tag nucleic acid sequence is identical;
   (d) the overall number of A+G nucleotides in each of the of the tag nucleic acid sequences is even; and
   (e) each member of the set of tag nucleic acids is comprised of a single nucleic acid sequence from the set of nucleic acid tags.

9. A set of tag nucleic acids according to claim 8, wherein each tag nucleic acid sequence comprises a constant region and a variable region, wherein no two members of the set can be aligned with less than two errors in the variable region, wherein an error is either a mismatch hybridization or an overhanging nucleotide and each member of the set of tag nucleic acids is comprised of a single nucleic acid sequence from the set of nucleic acid tags.

10. The set of tag nucleic acids of claim 9, wherein:
   (a) the total number of nucleotides in each tag nucleic acid sequence is identical;
   (b) the number of G+C nucleotides in each tag nucleic acid sequence is identical; and,
   (c) the overall number of A+G nucleotides in each of the variable regions of the tag nucleic acid sequences is even, and
   (d) each member of the set of tag nucleic acids is comprised of a single nucleic acid sequence from the set of nucleic acid tags.

* * * * *

UNITED STATES PATENT AND TRADEMARK OFFICE
CERTIFICATE OF CORRECTION

PATENT NO. : 6,458,530 B1
DATED : October 1, 2002
INVENTOR(S) : Macdonald S. Morris et al.

It is certified that error appears in the above-identified patent and that said Letters Patent is hereby corrected as shown below:

Column 54,
Line 28, please delete "mothod of 104." and insert therein -- method of claim 1. --.

Signed and Sealed this

Twenty-second Day of March, 2005

JON W. DUDAS
*Director of the United States Patent and Trademark Office*